(12) United States Patent
Colavito et al.

(10) Patent No.: US 11,071,626 B2
(45) Date of Patent: Jul. 27, 2021

(54) DIAMETRIC EXPANSION FEATURES FOR PROSTHETIC VALVES

(71) Applicant: W. L. Gore & Associates, Inc., Newark, DE (US)

(72) Inventors: Kyle W. Colavito, Flagstaff, AZ (US); Dustin V. Dienno, Flagstaff, AZ (US); Paul D. Goodman, Flagstaff, AZ (US); Brandon C. Hedberg, Flagstaff, AZ (US); Brandon A. Lurie, Flagstaff, AZ (US); Devin M. Nelson, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 102 days.

(21) Appl. No.: 16/355,515

(22) Filed: Mar. 15, 2019

(65) Prior Publication Data

US 2019/0282360 A1   Sep. 19, 2019

Related U.S. Application Data

(60) Provisional application No. 62/644,156, filed on Mar. 16, 2018.

(51) Int. Cl.
 *A61F 2/24* (2006.01)
 *F16K 15/14* (2006.01)
(52) U.S. Cl.
 CPC .......... *A61F 2/2418* (2013.01); *A61F 2/2412* (2013.01); *A61F 2/2415* (2013.01);
 (Continued)

(58) Field of Classification Search
 CPC ........ A61F 2/24; A61F 2/2409; A61F 2/2412; A61F 2/2418
 See application file for complete search history.

(56) References Cited

U.S. PATENT DOCUMENTS

| | | | |
|---|---|---|---|
| 2008/0114452 A1 | 5/2008 | Gabbay | |
| 2013/0046373 A1* | 2/2013 | Cartledge | A61F 2/2439 623/1.11 |

(Continued)

FOREIGN PATENT DOCUMENTS

| | | |
|---|---|---|
| EP | 2853237 A1 | 4/2015 |
| WO | 2012/018779 A2 | 2/2012 |

(Continued)

OTHER PUBLICATIONS

International Search Report and Written Opinion received for PCT Patent Application No. PCT/US2019/022646, dated Aug. 6, 2019, 19 pages.

*Primary Examiner* — Suba Ganesan

(57) ABSTRACT

Various features and associated advantages are described for diametrically adjustable support structures, adjustable valve structures, removable/replaceable valve structures, and associated systems and methods. Although some examples are directed toward prosthetic valve that is a conduit having a valve structure, or a "valved conduit" (e.g., used to replace a pulmonary valve and a portion of the corresponding pulmonary artery or an aortic valve and the aortic root), and other examples are directed toward prosthetic valves implanted native valve orifices (e.g., to replace an aortic or mitral valve), the features and advantages of the structures associated with those examples are interchangeable regardless of a particular application for which the examples are described.

22 Claims, 19 Drawing Sheets

(52) U.S. Cl.
CPC .......... *A61F 2/2475* (2013.01); *F16K 15/147* (2013.01); *A61F 2240/001* (2013.01); *A61F 2250/001* (2013.01); *A61F 2250/0071* (2013.01); *A61F 2250/0082* (2013.01)

(56) References Cited

U.S. PATENT DOCUMENTS

| | | | |
|---|---|---|---|
| 2014/0188219 A1* | 7/2014 | Conklin | A61F 2/2445 623/2.17 |
| 2015/0202065 A1 | 7/2015 | Shalev | |
| 2016/0220361 A1* | 8/2016 | Weber | A61F 2/2412 |
| 2017/0000603 A1* | 1/2017 | Conklin | A61F 2/2409 |
| 2018/0289475 A1* | 10/2018 | Chung | A61F 2/2445 |
| 2018/0325651 A1* | 11/2018 | Sumanasinghe | A61F 2/07 |
| 2019/0083255 A1* | 3/2019 | Najm | A61F 2/91 |
| 2019/0133764 A1* | 5/2019 | Carr | A61F 2/2418 |
| 2019/0388221 A1* | 12/2019 | Lee | A61F 2/2436 |

FOREIGN PATENT DOCUMENTS

| | | |
|---|---|---|
| WO | 2015/168508 A2 | 11/2015 |
| WO | 2017/137868 A1 | 8/2017 |

\* cited by examiner

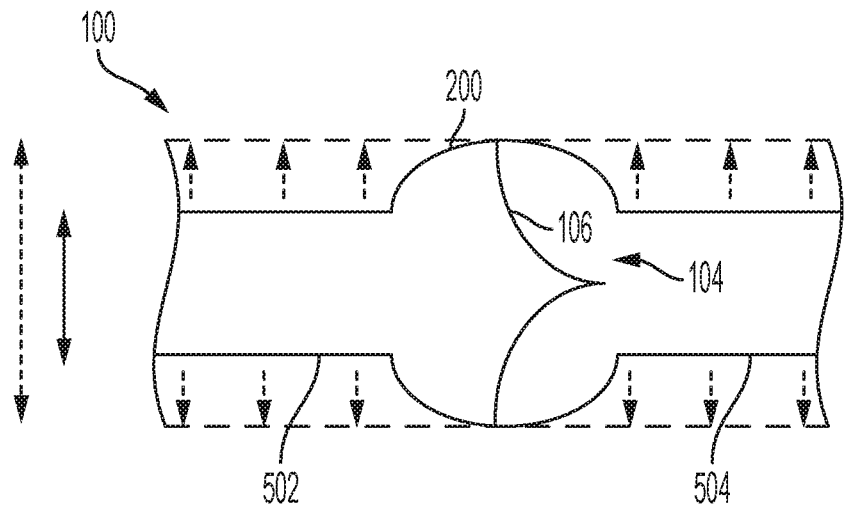
FIG. 21
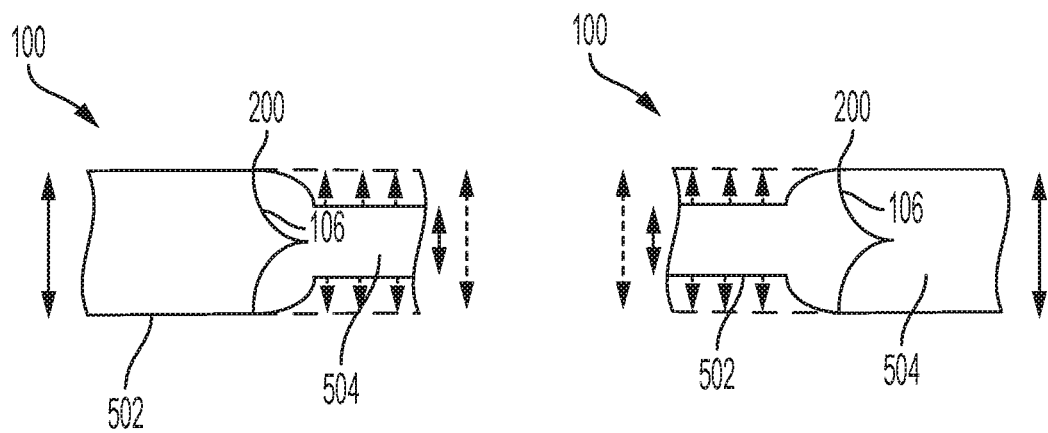
FIG. 22
FIG. 23

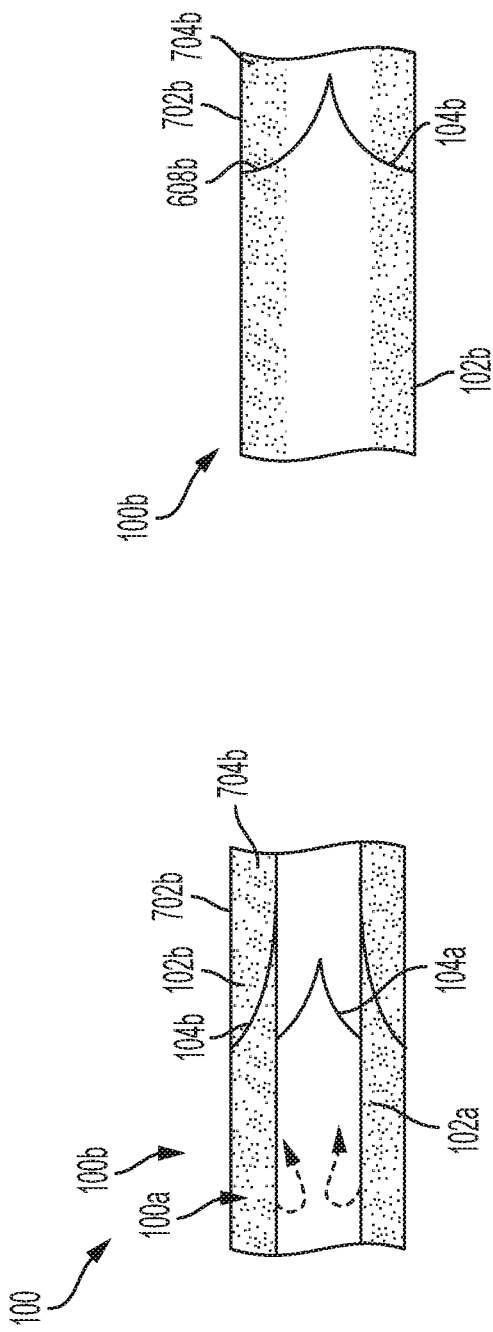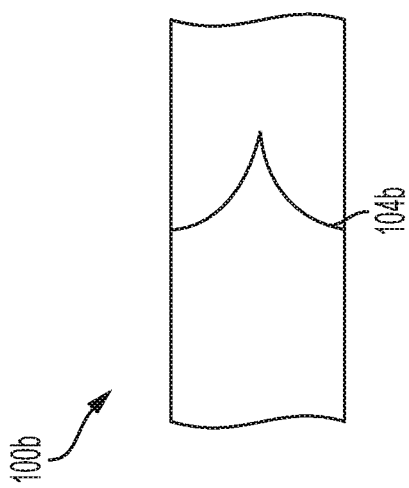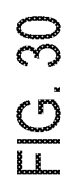

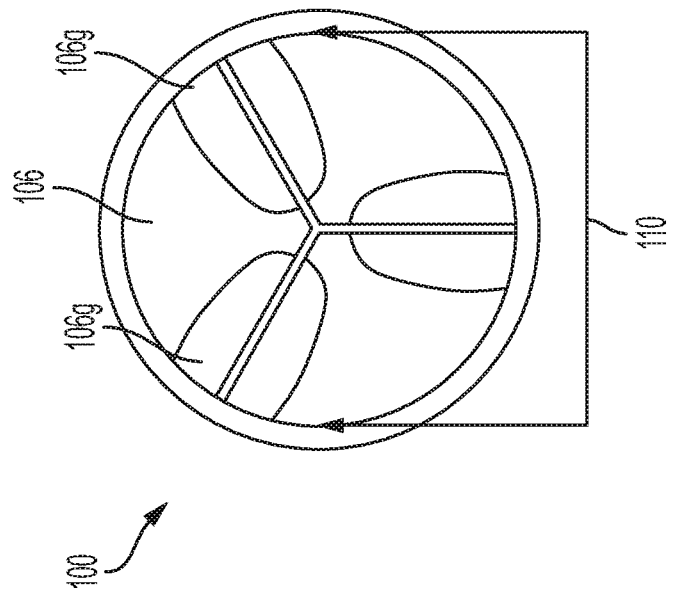
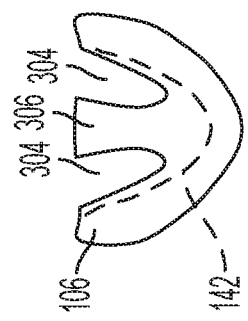
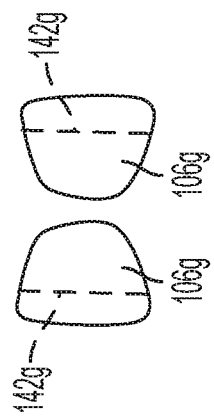
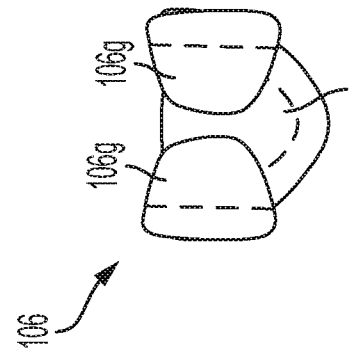

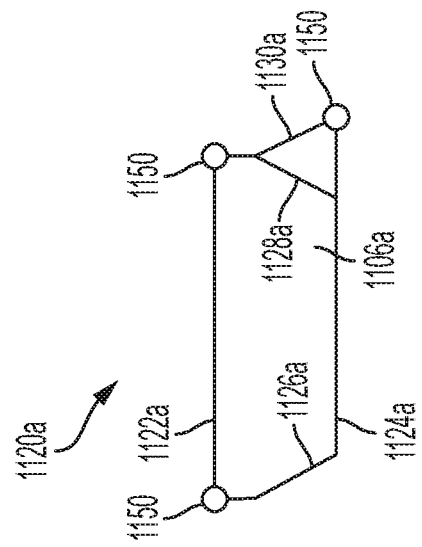
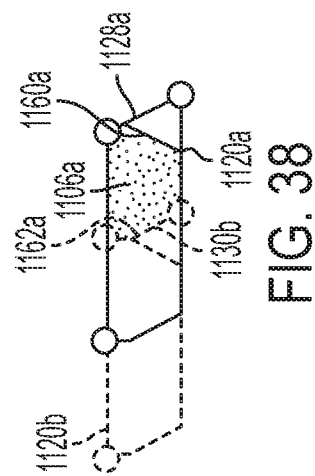
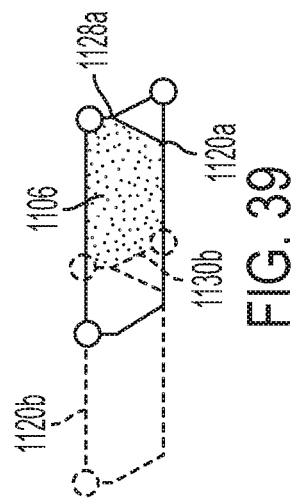
FIG. 37
FIG. 38
FIG. 39
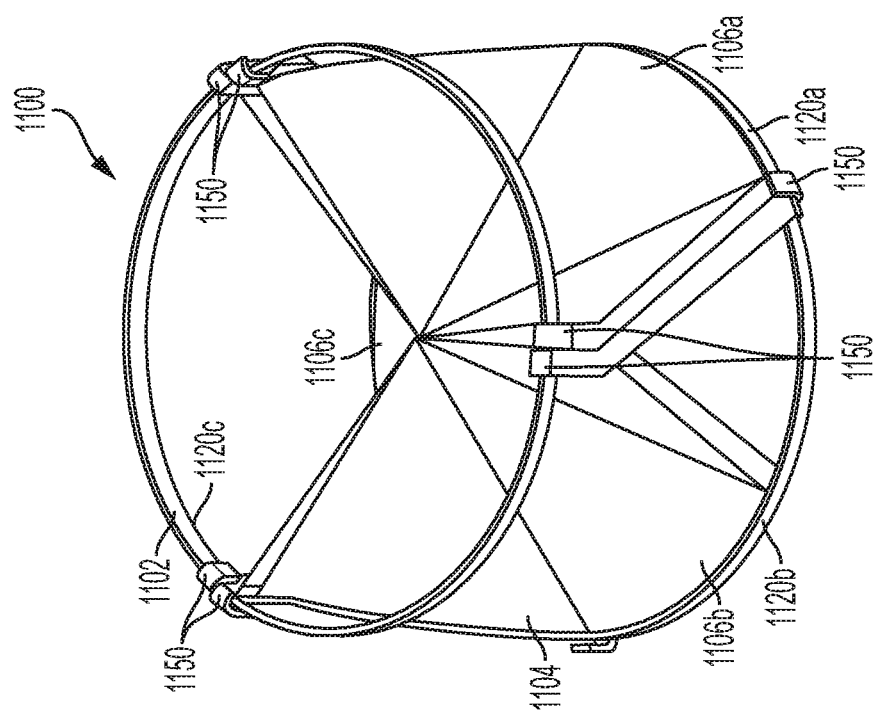
FIG. 36

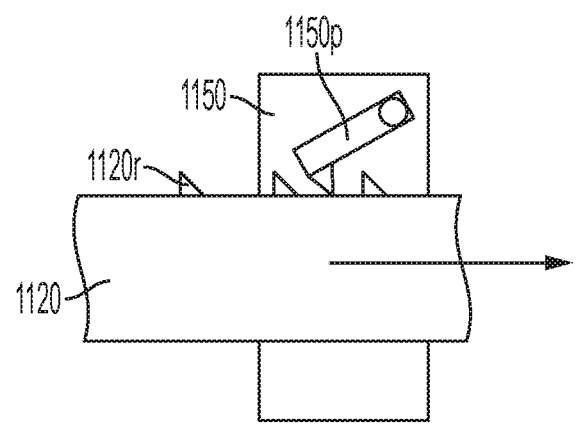
FIG. 43
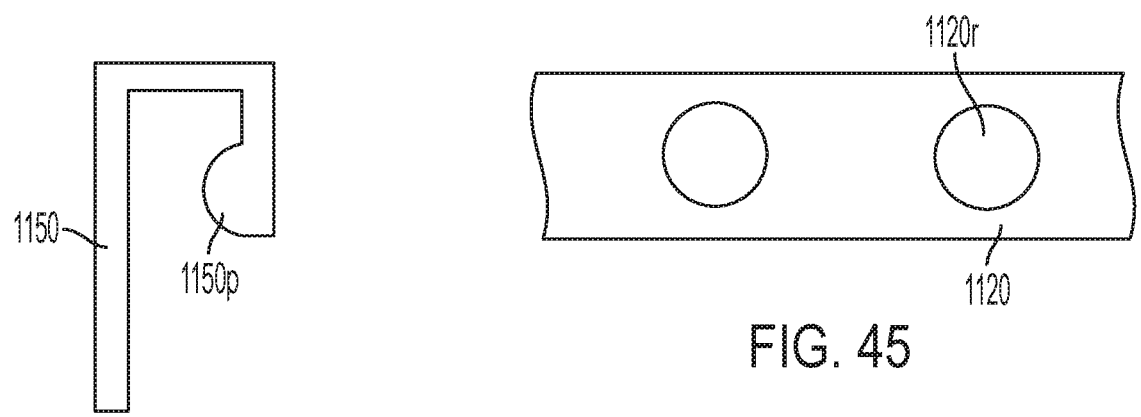
FIG. 44
FIG. 45

DIAMETRIC EXPANSION FEATURES FOR PROSTHETIC VALVES

CROSS-REFERENCE TO RELATED APPLICATION

This application claims the benefit of Provisional Application No. 62/644,156, filed Mar. 16, 2018, which is incorporated herein by reference in its entirety for all purposes.

BACKGROUND

Prosthetic valves have been developed that attempt to mimic the function and performance of a native valve. One or more flexible leaflets are generally coupled to a support structure that supports the leaflets and provides dimensional stability to the implanted prosthetic valve.

In operation, the leaflets of such prosthetic valves open when the upstream fluid pressure exceeds the downstream fluid pressure on the valve and close when the downstream fluid pressure exceeds the upstream fluid pressure on the valve. Generally, the free edges of the leaflets coapt under the influence of downstream fluid pressure closing the prosthetic valve to prevent downstream blood from flowing retrograde through the prosthetic heart valve.

Various situations arise in which the requisite diametric profile of a prosthetic valve changes from one point in time to another. For example, in pediatric applications, a valve of a first, smaller inner diameter (i.e., the inner flow diameter) may be appropriate, but following growth of the patient, a larger inner diameter for the prosthetic valve is desirable. The removal of an existing valve and/or implantation of another valve with a larger flow diameter may give rise to various complications and concomitant risks.

SUMMARY

Described embodiments are directed to apparatuses, systems, and methods for valved conduits.

According to one example ("Example 1"), a prosthetic valve includes one or more primary leaflets, and one or more auxiliary leaflets stored in an inactive state, the one or more auxiliary leaflets being configured to release to an active state upon diametrically expanding the prosthetic valve.

According to another example ("Example 2"), further to Example 1, the one or more auxiliary leaflets are stored in the inactive state by one or more folds formed by the one or more primary leaflets, the one or more folds of the primary leaflets being releasably secured in a folded configuration and configured to be released from the folded configuration upon diametrically expanding the prosthetic valve to transition the auxiliary leaflets to the active state.

According to another example ("Example 3"), further to Example 2, at least one of the primary leaflets includes a first side region, a second side region, and a central region located between the first and second side regions, and wherein the one or more folds are formed in at least one of the first side region, the second side region, and the central region.

According to another Example ("Example 4"), further to Example 3 or Example 4, the one or more folds formed by the one or more primary leaflets are releasably secured in the folded configuration by a coating, an adhesive, a thermal bond, a mechanical fastener, or combinations thereof.

According to another Example ("Example 5"), further to any one of Examples 2-4, the one or more folds formed by the one or more primary leaflets are releasably secured in the folded configuration such that the folds formed by the primary leaflets are configured to be released from the folded configuration upon an expansion force being imparted on the prosthetic valve and/or following an extended period of time.

According to another Example ("Example 6"), further to any one of Examples 2-5, the one or more primary leaflets include a pair of adjacent primary leaflets and the one or more folds formed by the primary leaflets are positioned at a location corresponding to a commissure region between pair of adjacent primary leaflets.

According to another Example ("Example 7"), further to any one of Examples 1-6, the prosthetic valve includes a support structure to which the one or more primary leaflets are coupled.

According to another Example ("Example 8"), further to Example 7, the support structure includes a tubular conduit.

According to another Example ("Example 9"), further to Example 7 or Example 8, wherein the support structure includes a frame.

According to another Example ("Example 10"), further to any one of Examples 7-9, the one or more auxiliary leaflets are stored in the inactive state by one or more folds formed by the support structure, the folds of the support structure each being releasably secured in a folded configuration and configured to be released from the folded configuration upon diametrically expanding the prosthetic valve to transition the auxiliary leaflets to the active state.

According to another Example ("Example 11"), further to Example 10, the one or more folds formed by the support structure are releasably secured in the folded configuration by a coating, an adhesive, a thermal bond, a mechanical fastener, or combinations thereof.

According to another Example ("Example 12"), further to Examples 10 or 11, the one or more folds formed by the support structure are releasably secured in the folded configuration such that the folds formed by the support structure are configured to release from the folded configuration upon an expansion force being imparted on the prosthetic valve and/or following an extended period of time.

According to another Example ("Example 13"), further to any one of Examples 10 or 11, the one or more primary leaflets include a pair of adjacent primary leaflets and the one or more folds formed by the support structure are positioned at a location along the support portion corresponding to a commissure region between the pair of adjacent primary leaflets.

According to another Example ("Example 14"), the prosthetic valve of any preceding Example, the primary leaflets include a pair of adjacent, primary leaflets coupled to a splittable commissure support, and further wherein one of the auxiliary leaflets is coupled to the splittable commissure support such that the auxiliary leaflet is transitionable from the stored, inactive state to the released, active state upon diametrically expanding the prosthetic valve to split the splittable commissure support.

According to another Example ("Example 15"), further to Example 14, the splittable commissure support is releasably secured together by a coating, an adhesive, a thermal bond, a mechanical fastener, or combinations thereof.

According to another Example ("Example 16"), further to any one of Examples 14-15, the releasable commissure support is configured to be released and split upon an expansion force being imparted on the prosthetic valve and/or following an extended period of time.

According to another Example ("Example 17"), further to any preceding Examples, the prosthetic valve has a first operative diameter at which the prosthetic valve is configured to be implanted and a second operative diameter that is larger than the first operative diameter to which the prosthetic valve is configured to be diametrically adjusted, and further wherein the one or more of primary leaflets are operable to move between open and closed positions to allow and inhibit flow, respectively, through the prosthetic valve such that the primary leaflets are configured in an active state, and further wherein the prosthetic valve is configured such that upon transitioning to the second operative diameter the one or more auxiliary leaflets are transitioned to the active state such that the auxiliary leaflets are operable to move between open and closed positions to allow and inhibit flow, respectively, through the prosthetic valve.

According to another Example ("Example 18"), further to Example 17, the one or more primary leaflets are configured to be in the active state when the prosthetic valve is at the second operative diameter.

According to another Example ("Example 19"), a method of making a prosthetic valve includes forming a valve structure including one or more primary leaflets and one or more auxiliary leaflets, associating the valve structure with a support structure, and storing the one or more auxiliary leaflets in an inactive state such that the one or more auxiliary leaflets are configured to release to an active state upon diametrically expanding the prosthetic valve.

According to another Example ("Example 20"), further to the method of Example 19, the prosthetic valve is configured to be transitioned from a first operative diameter at which the prosthetic valve is configured to be implanted to a second operative diameter that is larger than the first operative diameter, and further wherein the one or more primary leaflets are operable to move between open and closed positions to allow and inhibit flow, respectively, through the prosthetic valve such that the primary leaflets are configured in an active state when the prosthetic valve is at the first operative diameter, and further wherein the prosthetic valve is configured such that upon transitioning to the second operative diameter the one or more auxiliary leaflets are transitioned from the inactive state to the active state such that the one or more auxiliary leaflets are operable to move between open and closed positions to allow and inhibit flow, respectively, through the prosthetic valve.

According to another Example ("Example 21"), further to the method of Examples 19 or 20, storing the one or more auxiliary leaflets in the inactive state includes storing the one or more auxiliary leaflets in one or more folds formed by the one or more primary leaflets, a support structure of the prosthetic valve, or both.

According to another Example ("Example 22") further to the method of Example 21, storing the one or more auxiliary leaflets in the inactive state further includes releasably securing the one or more folds in a folded configuration using a coating, an adhesive, a thermal bond, a mechanical fastener, or combinations thereof.

According to another Example ("Example 23"), a method of diametrically adjusting a prosthetic valve includes transitioning a prosthetic valve from a first operative diameter at which the prosthetic valve is configured to be implanted to a second operative diameter that is larger than the first operative diameter, the first operative diameter including one or more primary leaflets of the prosthetic valve being operable to move between open and closed positions to allow and inhibit flow, respectively, through the prosthetic valve such that the primary leaflets are configured in an active state when the prosthetic valve is at the first operative diameter, the first operative diameter further including one or more auxiliary leaflets of the prosthetic valve being stored in an inactive state in which the auxiliary leaflets are inoperable to inhibit flow through the valve, and the second operative diameter including the one or more auxiliary leaflets being transitioned from the inactive state to an active state in which the one or more auxiliary leaflets are operable to move between open and closed positions to allow and inhibit flow, respectively, through the prosthetic valve.

According to another Example ("Example 24"), further to the method of Example 23, at the first operative diameter the one or more auxiliary leaflets are stored in the inactive state by one or more folds formed by the one or more primary leaflets, the one or more folds of the primary leaflets being releasably secured in a folded configuration and configured to be released from the folded configuration upon diametrically expanding the prosthetic valve to transition the one or more auxiliary leaflets to the active state, and further wherein transitioning a prosthetic valve from a first operative diameter to a second operative diameter includes releasing the one or more folds of the primary leaflets.

According to another Example ("Example 25"), further to the method of Example 24, at least one of the one or more primary leaflets includes a first side region, a second side region, and a central region located between the first and second side regions, and wherein at the first operative diameter the one or more folds of the primary leaflets are formed in at least one of the first side region, the second side region, and the central region.

According to another Example ("Example 26"), further to the method of Example 24, the one or more folds formed by the one or more leaflets are releasably secured in the folded configuration by a coating, an adhesive, a thermal bond, a mechanical fastener, or combinations thereof.

According to another Example ("Example 27"), further to the method of Example 24, the one or more folds formed by the one or more primary leaflets are released from the folded configuration by imparting an expansion force on the prosthetic valve and/or following an extended period of time in a body of a patient.

According to another Example ("Example 28"), further to the method of Example 24, the one or more primary leaflets include a pair of adjacent, primary leaflets coupled to a splittable commissure support, and further wherein one of the auxiliary leaflets is coupled to the splittable commissure support, the method further comprising transitioning the auxiliary leaflet coupled to the commissure support from the stored, inactive state to the released, active state by splitting the splittable commissure support.

According to another Example ("Example 29"), a prosthetic valve includes one or more leaflets, the leaflets define a contained portion and an uncontained portion that is exposed to a fluid flow through the valve when the valve defines a first diameter at which the prosthetic valve is configured to be implanted, and wherein the contained portion becomes uncontained and exposed to a fluid flow through the valve when the valve defines a second diameter that is larger than the first diameter.

According to another Example ("Example 30"), further to the prosthetic valve of Example 29, further includes a support structure defining an upstream end and a downstream end, the valve structure being arranged within the support structure such that the valve structure is configured to allow flow in upstream end out of the downstream end while inhibiting flow from the downstream end out the upstream end.

According to another Example ("Example 31"), further to the prosthetic valve of Example 30, the support structure includes a compression layer in which the contained portion is stored, the compression layer being configured to be collapsed upon expansion of the prosthetic valve from the first diameter to the second diameter such that the contained portion is exposed from the compression layer.

According to another Example ("Example 32"), further to Example the prosthetic valve of Example 31, the support structure includes an inner layer, an outer layer, and the compression layer is located between the inner layer and the outer layer to define a compressible space, the inner layer being configured to expand outwardly against the compression layer under a radial expansion force while the outer layer resists outward deformation such that the compression layer is radially collapsed.

According to another Example ("Example 33"), further to Examples 31 or 32, the compression layer includes one or more biasing elements.

According to another Example ("Example 34"), further to any one of Example 31 to 33, the compression layer includes a compressible material.

According to another Example ("Example 35"), further to Example 30, the contained portion is releasably secured to the support structure at the first diameter and is configured to be released from the support structure when the valve structure is transitioned to the second diameter.

According to another Example ("Example 36"), further to Example 29, the contained portion is releasably secured to the exposed portion at the first diameter and is configured to be released when the valve structure is transitioned to the second diameter.

According to another Example ("Example 37"), a method of making a prosthetic valve includes forming a valve structure including one or more leaflets, and arranging the valve structure within a support structure, the valve structure being arranged within the support structure such that the valve structure is configured to allow flow in upstream end out of the downstream end while inhibiting flow from the downstream end out the upstream end, wherein the leaflets define a contained portion and an uncontained portion that is exposed to a fluid flow through the valve when the valve defines a first diameter at which the prosthetic valve is configured to be implanted, and wherein the contained portion is configured to become uncontained and exposed to a fluid flow through the valve when the valve is transitioned to a second diameter that is larger than the first diameter.

According to another Example ("Example 38"), further to the method of Example 37, the method also includes storing the contained portion within a compression layer of the support structure, the compression layer being configured to be collapsed upon expansion of the prosthetic valve from the first diameter to the second diameter such that the contained portion is exposed from the compression layer.

According to another Example ("Example 39"), further to the method of Example 38, the method also includes providing the support structure with an inner layer and an outer layer such that the compression layer is located between the inner layer and the outer layer to define a compressible space, the inner layer being configured to expand outwardly against the compression layer under a radial expansion force while the outer layer resists outward deformation such that the compression layer is radially collapsed.

According to another Example ("Example 40"), further to the method of Example 39, the compression layer includes one or more biasing elements that maintain spacing between the inner layer and the outer layer.

According to another Example ("Example 41"), further to the method of any one of Examples 38-40, the compression layer includes a compressible material.

According to another Example ("Example 42"), further to the method of any one of Example 38, the method also includes releasably securing the contained portion to the support structure at the first diameter such that the contained portion is configured to be released from the support structure when the valve structure is transitioned to the second diameter.

According to another Example ("Example 43"), a prosthetic valve includes a support structure, and a valve structure coupled to the support structure, the valve structure including, one or more primary leaflets, and one or more secondary leaflets adjacent to the primary leaflets, wherein the primary leaflets function to inhibit flow in a first direction and allow flow in a second direction through the prosthetic valve and the secondary leaflets are not functional to inhibit flow in the first direction and allow flow in the second direction through the prosthetic valve when the prosthetic valve is at a first diameter at which the prosthetic valve is configured to be implanted, wherein the prosthetic valve is configured to be transitioned to a second diameter that is larger than the first diameter, and wherein the prosthetic valve is configured such that the primary leaflets and the secondary leaflets function to inhibit flow in the first direction and allow flow in the second direction through the prosthetic valve after the prosthetic valve is transitioned to the second state.

According to another Example ("Example 44"), a prosthetic valve includes a support structure, and a valve structure coupled to the support structure, the valve structure including, one or more leaflets including a central region and two side regions on opposite sides of the central region, wherein the central region is configured to be active and the two side regions are configured to be inactive when the prosthetic valve is at a first diameter at which the prosthetic valve is configured to be implanted such that the valve structure operates to inhibit flow in a first direction and allow flow in a second direction through the prosthetic valve at the first diameter and further wherein the central region and the two side regions are configured to be active when the prosthetic valve is at a second diameter that is larger than the first diameter such that the valve structure operates to inhibit flow in the first direction and allow flow in the second direction through the prosthetic valve at the second diameter.

According to another Example ("Example 45"), further to the prosthetic valve of Example 44, the two side regions are releasably folded such that the two side regions are inactive.

According to another Example ("Example 46"), further to the prosthetic valve of Examples 44 or 45, the support structure comprises a conduit having an inner surface, and further wherein the two side regions are releasably coupled to the inner surface of the conduit such that the two side regions are inactive and the two side regions are releasable from the conduit when the prosthetic valve is expanded to the second diameter.

According to another Example ("Example 47"), a method of making a prosthetic valve includes coupling a valve structure to a support structure, the valve structure including, one or more leaflets including a central region and two side regions on opposite sides of the central region, wherein the central region is configured to be active and the two side regions are configured to be inactive when the prosthetic valve is at a first diameter at which the prosthetic valve is configured to be implanted such that the valve structure operates to inhibit flow in a first direction and allow flow in a second direction through the prosthetic valve at the first diameter and further wherein the central region and the two side regions are configured to be active when the prosthetic valve is at a second diameter that is larger than the first diameter such that the valve structure operates to inhibit flow in the first direction and allow flow in the second direction through the prosthetic valve at the second diameter.

According to another Example ("Example 48"), further to the method of Example 47, the method includes the two side regions are folded in the inactive state.

According to another Example ("Example 49"), further to the method of Example 47, the method includes the support structure comprises a conduit having an inner surface, the method further comprising folding the two side regions and coupling the two side regions to the inner surface of the conduit such that the two side regions are releasable from the conduit when the prosthetic valve is expanded to the second diameter.

According to another Example ("Example 50"), a prosthetic valve includes a support structure, and a valve structure coupled to the support structure, the valve structure including, one or more leaflets including a central region and two side regions on opposite sides of the central region, wherein the central region is releasably folded to define an overlapping region such that the valve structure operates to inhibit flow in a first direction and allow flow in a second direction through the prosthetic valve at a first diameter at which the prosthetic valve is configured to be implanted and wherein the overlapping region is releasable such that the central portion is unfolded and the valve structure operates to inhibit flow in the first direction and allow flow in the second direction through the prosthetic valve at a second diameter that is larger than the first diameter.

According to another Example ("Example"), a method of making a prosthetic valve includes coupling a support structure to a valve structure, the valve structure including one or more leaflets including a central region and two side regions on opposite sides of the central region, wherein the central region is releasably folded to define an overlapping region such that the valve structure operates to inhibit flow in a first direction and allow flow in a second direction through the prosthetic valve at a first diameter at which the prosthetic valve is configured to be implanted and wherein the overlapping region is releasable such that the central portion is unfolded and the valve structure operates to inhibit flow in the first direction and allow flow in the second direction through the prosthetic valve at a second diameter that is larger than the first diameter.

According to another Example ("Example"), a prosthetic valve includes a support structure, and a valve structure coupled to the support structure, the valve structure including, one or more leaflets including a central region and two side regions on opposite sides of the central region, wherein the side regions are releasably folded defining an overlapping region such that the valve structure operates to inhibit flow in a first direction and allow flow in a second direction through the prosthetic valve at a first diameter at which the prosthetic valve is configured to be implanted and wherein the overlapping region is releasable such that the side regions are unfolded and the valve structure operates to inhibit flow in the first direction and allow flow in the second direction through the prosthetic valve at a second diameter that is larger than the first diameter.

According to another Example ("Example 53"), a method of making a prosthetic valve, the method includes coupling a support structure to a valve structure, the valve structure including one or more leaflets including a central region and two side regions on opposite sides of the central region, wherein the side regions are releasably folded defining an overlapping region such that the valve structure operates to inhibit flow in a first direction and allow flow in a second direction through the prosthetic valve at a first diameter at which the prosthetic valve is configured to be implanted and wherein the overlapping region is releasable such that the side regions are unfolded and the valve structure operates to inhibit flow in the first direction and allow flow in the second direction through the prosthetic valve at a second diameter that is larger than the first diameter.

According to another Example ("Example 54"), a prosthetic valve a first leaflet component, and a second leaflet component at least partially overlapping the first leaflet component to define an overlap region having a width, the first leaflet component and the second leaflet component configured to be in operable engagement with one another when the prosthetic valve is at a first diameter at which the prosthetic valve is configured to be implanted to allow fluid flow through the prosthetic valve in a first direction and inhibit fluid flow through the prosthetic valve in an opposite, second direction, and the first leaflet component and the second leaflet component being configured to be in operable engagement with one another when the prosthetic valve is at a second diameter that is larger than the first diameter by sliding relative to each other thereby reducing the width of the overlap region as the diameter of the prosthetic valve is increased, such that the first and second leaflet components allow fluid flow through the prosthetic valve in the first direction and inhibit fluid flow through the prosthetic valve in the opposite, second direction when the prosthetic valve is at the second, larger diameter.

According to another Example ("Example 55"), further to the prosthetic valve of Example 54, the prosthetic valve includes the first leaflet component includes a cut out at a side region of the first leaflet component to assist with diametric expansion of the first leaflet component.

According to another Example ("Example 56"), further to the prosthetic valve of Example 55, the prosthetic valve includes the second leaflet component overlaps cut out in the side region of the first leaflet component.

According to another Example ("Example 57"), further to the prosthetic valve of any one of Examples 54-56, the prosthetic valve includes the second leaflet component is located downstream of the first leaflet component.

According to another Example ("Example 58"), further to the prosthetic valve of any one of Examples 54-57, the prosthetic valve further includes another second leaflet component that is disposed downstream of and at least partially overlapping with the first leaflet component.

According to another Example ("Example 59"), further to the prosthetic valve of any one of Examples 54-58, the prosthetic valve further includes a support structure, wherein the first leaflet component and the second leaflet component are coupled to the support structure.

According to another Example ("Example 60"), a method of making a prosthetic valve, the method includes coupling a support structure to a valve structure, the valve structure including, a first leaflet component, and a second leaflet component at least partially overlapping the first leaflet component to define an overlap region having a width, the first leaflet component and the second leaflet component configured to be in operable engagement with one another when the prosthetic valve is at a first diameter at which the prosthetic valve is configured to be implanted to allow fluid flow through the prosthetic valve in a first direction and inhibit fluid flow through the prosthetic valve in an opposite, second direction, and the first leaflet component and the second leaflet component being configured to be in operable engagement with one another when the prosthetic valve is at a second diameter that is larger than the first diameter by sliding relative to each other thereby reducing the width of the overlap region as the diameter of the prosthetic valve is increased, such that the first and second leaflet components allow fluid flow through the prosthetic valve in the first direction and inhibit fluid flow through the prosthetic valve in the opposite, second direction when the prosthetic valve is at the second, larger diameter.

According to another Example ("Example 61"), a prosthetic valve includes a diametrically adjustable frame comprising a plurality of frame elements slidably engaged with one another, and a plurality of leaflets coupled to the diametrically adjustable frame, each of the leaflets being secured to a respective one of the frame elements such that stored leaflet material is stored in an inactive state when the adjustable frame is at a first diameter at which the prosthetic valve is configured to be implanted, each of the leaflets defining a first active size at the first diameter such that the leaflets allow fluid flow through the prosthetic valve in a first direction and inhibit fluid flow through the prosthetic valve in an opposite, second direction, the adjustable frame being transitionable to a second diameter that is larger than the first diameter by sliding the plurality of frame elements relative to one another to diametrically enlarge the diametrically adjustable frame and such that the stored leaflet material is paid out to enlarge the active size of the each of the leaflets to a second active size as the adjustable frame is diametrically enlarged to the second diameter, and such that each of the leaflets allow fluid flow through the prosthetic valve in the first direction and inhibit fluid flow through the prosthetic valve in the opposite, second direction at the second active size.

According to another Example ("Example 62"), further to the prosthetic valve of Example 61, each of the plurality of frame elements include tabs for slidably engaging another one of the plurality of frame elements.

According to another Example ("Example 63"), further to the prosthetic valve of Examples 61-62, each of the frame elements includes a top rail, a bottom rail, a leaflet payout edge support, a primary leaflet edge support and a secondary leaflet edge support.

According to another Example ("Example 64"), further to the prosthetic valve of Example 63, each leaflet is secured to a corresponding one of the plurality frame elements, where each leaflet is secured to the leaflet payout edge support and the primary leaflet edge support of the corresponding one of the plurality of frame elements such that the primary leaflet edge support of the corresponding one of the plurality of frame elements serves to define a first operative edge of the leaflet and the secondary leaflet edge support of another one of the plurality of frame elements serves to define a second operative edge of the leaflet that is opposite the first operative edge of the leaflet.

According to another Example ("Example 65"), further to the prosthetic valve of any one of Examples 61-64, the frame elements are axi-symmetric.

According to another Example ("Example 66"), further to the prosthetic valve of any one of Examples 61-65, the diametrically adjustable frame includes retaining features configured act as stops that limit relative sliding of the plurality of frame elements at one or more pre-selected diameters of the adjustable frame.

According to another Example ("Example 67"), a method of making a prosthetic valve, the method includes securing a plurality of adjustable frame elements of an adjustable frame together such that the plurality of adjustable frame elements are slidable relative to one another to adjust a diameter of the adjustable frame from a first diameter at which the prosthetic valve is configured to be implanted to a second diameter that is larger than the first diameter, and coupling a plurality of leaflets to the diametrically adjustable frame with each of the leaflets being secured to a corresponding one of the frame elements such that stored leaflet material is stored in an inactive state when the adjustable frame is at a first diameter and each of the leaflets defines a first active size at the first diameter such that the leaflets allow fluid flow through the prosthetic valve in a first direction and inhibit fluid flow through the prosthetic valve in an opposite, second direction and such that upon transitioning the adjustable frame to the second diameter by sliding the plurality of frame elements relative to one another the stored leaflet material is paid out to enlarge the active size of the each of the leaflets to a second active size at which each of the leaflets allow fluid flow through the prosthetic valve in the first direction and inhibit fluid flow through the prosthetic valve in the opposite, second direction.

According to another Example ("Example 68"), further to the method of Example 67, each of the plurality of frame elements include tabs, and further wherein securing a plurality of adjustable frame elements of an adjustable frame together further includes slidably coupling the adjustable frame elements together with the tabs.

According to another Example ("Example 69"), further to the method of Example 67 or Example 68, each of the frame elements includes a top rail, a bottom rail, a leaflet payout edge support, a primary leaflet edge support and a secondary leaflet edge support, wherein coupling a plurality of leaflets to the diametrically adjustable frame with each of the leaflets being secured to a corresponding one of the frame elements includes securing each leaflet to the corresponding one of the plurality frame elements such that each leaflet is secured to the leaflet payout edge support and the primary leaflet edge support of the corresponding one of the plurality of frame elements with the primary leaflet edge support of the corresponding one of the plurality of frame elements serving to define a first operative edge of the leaflet and the secondary leaflet edge support of another one of the plurality of frame elements serves to define a second operative edge of the leaflet that is opposite the first operative edge of the leaflet.

According to another Example ("Example 70"), further to the method of any one of Examples 67-69, the diametrically adjustable frame includes retaining features, the method further comprising engaging the retaining features of the diametrically adjustable frame to act as stops that limit relative sliding of the plurality of frame elements at one or more pre-selected diameters of the adjustable frame.

According to another Example ("Example 71"), a prosthetic valve includes a first diametrically adjustable frame element configured to support a valve structure, and a second diametrically adjustable frame element coupled to the first diametrically adjustable frame element, the second diametrically adjustable frame element including a selective expansion feature for reinforcement of the first diametrically adjustable frame element against compression at a first diameter at which the prosthetic valve is configured to be implanted and reinforcement of the first diametrically adjustable frame element against compression following diametric expansion of the first frame element to a second diameter that is larger than the first diameter.

According to another Example ("Example 72"), further to the prosthetic valve of Example 71, the selective expansion feature is configured to self-engage upon compression at the first diameter.

According to another Example ("Example 73"), further to the prosthetic valve of Example 71 or Example 72, the selective expansion feature has an undulating shape at the first diameter and more straight, less undulating shape at the second diameter.

According to another Example ("Example 74"), a method of making a prosthetic valve, the method includes coupling a first diametrically adjustable frame element to a second diametrically adjustable frame element, the first diametrically frame element being configured to support a valve structure and the second diametrically adjustable frame element including a selective expansion feature for reinforcement of the first diametrically adjustable frame element against compression at a first diameter at which the prosthetic valve is configured to be implanted and reinforcement of the first diametrically adjustable frame element against compression following diametric expansion of the first frame element to a second diameter.

According to another Example ("Example 75"), further to the method of Example 74, the selective expansion feature is configured to self-engage upon compression at the first diameter.

According to another Example ("Example 76"), further to the method of Example 74 or Example 75, the selective expansion feature has an undulating shape at the first diameter and more straight, less undulating shape at the second diameter.

According to another Example ("Example 77"), a prosthetic valve includes a smaller, first prosthetic valve having a first inner diameter and including a first support structure and a first valve structure in an active state such that the first valve structure is configured to allow fluid flow through the prosthetic valve in a first direction and inhibit fluid flow through the prosthetic valve in an opposite, second direction, and a larger, second prosthetic valve having a second inner diameter that is larger than the first inner diameter of the smaller, first prosthetic valve and including a second support structure and a second valve structure in an inactive state such that the second valve structure is inoperable to inhibit fluid flow through the prosthetic valve, wherein the smaller, first prosthetic valve is releasably secured within the larger, second prosthetic valve such that the smaller, first prosthetic valve is configured to be released and removed from the larger, second prosthetic valve to transition the second valve structure to an active state in which the second valve structure is configured to allow fluid flow through the prosthetic valve in the first direction and inhibit fluid flow through the prosthetic valve in the opposite, second direction.

According to another Example ("Example 78") The prosthetic valve of Example 77, the smaller, first prosthetic valve is releasably secured within the larger, second prosthetic valve such that the smaller, first prosthetic valve is configured to be everted and peeled from within the larger, second prosthetic valve.

According to another Example ("Example 79"), further to the prosthetic valve of Example 77 or Example 78, the larger, second prosthetic valve includes a support layer and an intermediate layer disposed inside of the support layer, the intermediate layer being releasably coupled to the first support structure of the smaller, first prosthetic valve.

According to another Example ("Example 80"), further to the prosthetic valve of Example 79, the intermediate layer is configured to retain stored portions of the second valve structure such that the second valve structure is configured to initially operate at an initial inner diameter that approximates the first inner diameter of the smaller, first valve.

According to another Example ("Example 81"), further to the prosthetic valve of Example 80, the intermediate layer is compressible and/or removable over time to increase the initial inner diameter at which the second valve structure operates to the second inner diameter by releasing the stored portions of the second valve structure.

According to another Example ("Example 82"), a method of making a prosthetic valve, the method includes securing a smaller, first prosthetic valve within a larger, second prosthetic valve, the smaller, first prosthetic valve having a first inner diameter and including a first support structure and a first valve structure in an active state such that the first valve structure is configured to allow fluid flow through the prosthetic valve in a first direction and inhibit fluid flow through the prosthetic valve in an opposite, second direction and the larger, second prosthetic valve having a second inner diameter that is larger than the first inner diameter of the smaller, first prosthetic valve and including a second support structure and a second valve structure, the second valve structure being in an inactive state such that the second valve structure is inoperable to inhibit fluid flow through the prosthetic valve, wherein the smaller, first prosthetic valve is secured within the larger, second prosthetic valve such that the smaller, first prosthetic valve is releasable and removable from the larger, second prosthetic valve to transition a second valve structure from an inactive state to an active state in which the second valve structure is configured to allow fluid flow through the prosthetic valve in the first direction and inhibit fluid flow through the prosthetic valve in the opposite, second direction.

According to another Example ("Example 83"), further to the method of making the prosthetic valve of Example 82, the smaller, first prosthetic valve is releasably secured within the larger, second prosthetic valve such that the smaller, first prosthetic valve is configured to be everted and peeled from within the larger, second prosthetic valve.

According to another Example ("Example 84"), further to the method of making the prosthetic valve of Example 82 or Example 83, the larger, second prosthetic valve includes a support layer and an intermediate layer disposed inside of the support layer, the method further comprising releasably coupling the intermediate to the first support structure of the smaller, first prosthetic valve.

According to another Example ("Example 85"), further to the method of making the prosthetic valve of Example 84, the intermediate layer retains stored portions of the second valve structure such that the second valve structure is configured to initially operate at an initial inner diameter that approximates the first inner diameter of the smaller, first valve.

According to another Example ("Example 86"), further to the method of making the prosthetic valve of Example 85, the intermediate layer is compressible and/or removable over time to increase the initial inner diameter at which the second valve structure operates to the second inner diameter by releasing the stored portions of the second valve structure.

According to another Example ("Example 87"), a method of forming a prosthetic valve that is diametrically adjustable, the method comprising manufacturing a prosthetic valve at an initial, maximum diameter with a valve structure of the prosthetic valve configured to coapt, and then diametrically compacting the prosthetic valve to a smaller inner diameter at which the prosthetic valve is configured to be implanted such that the inner diameter of the prosthetic valve is decreased and portions of a valve structure of the prosthetic valve are reversibly attached to an inner surface of the prosthetic valve, where portions of the valve structure that are unattached to the inner surface of the prosthetic valve are configured to operatively coapt at the smaller diameter at which the prosthetic valve is configured to be implanted.

According to another Example ("Example 88"), a prosthetic valve includes a support structure having an inflow end and an outflow end, the support structure configured to be diametrically adjusted from a first diameter at which the prosthetic valve is configured to be implanted to a second diameter that is larger than the first diameter, the support structure including a support portion defining a base, a first leg, a second leg, a first commissure support, and a second commissure support, and a valve structure arranged within the support structure and coupled to the support portion of the support structure, the valve structure being configured to allow flow in a first direction through the prosthetic valve while inhibiting flow through the prosthetic valve in a second direction that is opposite the first direction when the support structure is at the first diameter and when the support structure is at the second diameter, the valve structure including one or more leaflets each having an attachment zone corresponding to a portion of the leaflet that is coupled to the support portion of the support structure, each leaflet defining a base, a free edge, a first commissure region, a second commissure region, and a belly region, and each leaflet being configured such that the free edge coapts at both the first diameter and the second diameter of the support structure.

According to another Example ("Example 89"), further to the prosthetic valve of Example 88, each leaflet is configured with sufficient material in the belly region to accommodate a reduction in overall height of the valve structure as the diameter of support structure increases.

According to another Example ("Example 90"), further to the prosthetic valve of Example 88 or Example 89, the support structure further includes a conduit portion, and further wherein the support portion is more resistant to diametric adjustment than the conduit portion, such that during diametric adjustment of the support structure deformation of the support structure occurs preferentially at the conduit portion.

According to another Example ("Example 91"), further to the prosthetic valve of any one of Examples 88-90, the support portion includes one or more resistant regions and one or more deformation regions that have relatively decreased resistance to the deformation regions such that preferential expansion during diametric adjustment of the support structure occurs preferentially in the one or more deformation regions of the support portion.

According to another Example ("Example 92"), further to the prosthetic valve of Example 91, the one or more resistant regions are more resistant to creep than the one or more deformation regions.

According to another Example ("Example 93"), further to the prosthetic valve of Example 91 or Example 92, the one or more resistant regions includes a coating, a surface treatment, a reinforcement element, or combinations thereof for enhancing resistance to deformation relative to the one or more deformation regions.

According to another Example ("Example 94"), a method of making a prosthetic valve, the method includes arranging a valve structure within a support structure, the support structure having an inflow end and an outflow end and being configured to be diametrically adjusted from a first diameter at which the prosthetic valve is configured to be implanted to a second diameter that is larger than the first diameter, the support structure including a support portion defining a base, a first leg, a second leg, a first commissure support, and a second commissure support, and coupling the valve structure to the support portion of the support structure, such that the valve structure is configured to allow flow in a first direction through the prosthetic valve while inhibiting flow through the prosthetic valve in a second direction that is opposite the first direction when the support structure is at the first diameter and when the support structure is at the second diameter, the valve structure including one or more leaflets each having an attachment zone corresponding to a portion of the leaflet that is coupled to the support portion of the support structure, each leaflet defining a base, a free edge, a first commissure region, a second commissure region, and a belly region, and each leaflet being configured such that the free edge coapts at both the first diameter and the second diameter of the support structure.

According to another Example ("Example 95"), further to the method of Example 94, each leaflet is coupled to the support structure such that each leaflet is configured with sufficient material in the belly region to accommodate a reduction in overall height of the valve structure as the diameter of support structure increases.

According to another Example ("Example 96"), further to the method of Example 94 or Example 95, the support structure further includes a conduit portion, and further wherein the support portion is more resistant to diametric adjustment than the conduit portion, such that during diametric adjustment of the support structure deformation of the support structure occurs preferentially at the conduit portion.

According to another Example ("Example 97"), further to the method of any one of Example 94-96, the support portion includes one or more resistant regions and one or more deformation regions that have relatively decreased resistance to the deformation regions such that preferential expansion during diametric adjustment of the support structure occurs preferentially in the one or more deformation regions of the support portion.

According to another Example ("Example 98"), further to the method of Example 97, the one or more resistant regions are more resistant to creep than the one or more deformation regions.

According to another Example ("Example 99"), further to the method of Example 97 or Example 98, the one or more resistant regions includes a coating, a surface treatment, a reinforcement element, or combinations thereof for enhancing resistance to deformation relative to the one or more deformation regions.

According to one example ("Example 100"), a prosthetic valve includes a plurality of primary leaflets, and one or more auxiliary leaflets stored in an inactive state, the secondary leaflets being configured to release to an active state upon diametrically expanding the prosthetic valve.

According to another example ("Example 101") further to Example 100, the auxiliary leaflets are stored in the inactive state by one or more folds in the primary leaflets and one or more folds in a support structure of the prosthetic valve.

According to another example ("Example 102"), a prosthetic valve includes a pair of adjacent, primary leaflets coupled to a splittable commissure support, and an auxiliary leaflet coupled to the splittable commissure support, wherein the auxiliary leaflet is transitionable from a stored, inactive state to a released active state upon diametrically expanding the prosthetic valve to split the splittable commissure support.

According to another example ("Example 103"), a prosthetic valve includes a plurality of leaflets, wherein the leaflets define a contained portion and an uncontained portion that is exposed to a fluid flow through the valve when the valve defines a first diameter, and wherein the contained portion becomes uncontained and exposed to a fluid flow through the valve when the valve defines a second diameter that is larger than the first diameter.

According to another example, ("Example 104"), a prosthetic valve includes a plurality of primary leaflets, and one or more secondary leaflets adjacent to one or more of the primary leaflets, wherein the secondary leaflet is operable to be non-functional in a first state wherein the valve is at a first diameter and functional in a second state wherein the valve is at a second diameter that is larger than the first diameter.

According to another example, ("Example 105"), a prosthetic valve includes a plurality of leaflets, each leaflet including a free edge and a base, wherein each leaflet includes a central region and two side regions on opposite sides of the central region, wherein the two side regions are operable to be inactive in a first state wherein the valve is at a first diameter and active in a second state wherein the valve is at a second diameter that is larger than the first diameter.

According to another example, ("Example 106"), further to Example 105, the two side regions are folded in the inactive state.

According to another example, ("Example 107"), further to Example 105, the prosthetic valve further includes a conduit, wherein the leaflets are adjacent an inner surface of the conduit, wherein the two side regions are folded and adhered to the conduit wherein the valve is at a first diameter and wherein the two side regions are released from the conduit wherein the valve is expanded to the second diameter.

According to another example, ("Example 108"), further to Example 105, the prosthetic valve further includes a conduit, wherein the leaflets are adjacent an inner wall of the conduit, wherein the two side regions are folded and adhered to the conduit wherein the valve is at a first diameter and wherein the two side regions are released from the conduit wherein the valve is at the second diameter.

According to another example, ("Example 109"), a prosthetic valve includes a plurality of leaflets, each leaflet including a free edge and a base, wherein each leaflet includes a central region and two side regions on opposite sides of the central region, wherein the central region is folded defining an overlapping region in a first state wherein the valve is at a first diameter and wherein the folded region is not folded in a second state wherein the valve is at a second diameter that is larger than the first diameter.

According to another example, ("Example 110"), a prosthetic valve includes a plurality of leaflets, each leaflet including a free edge and a base, wherein each leaflet includes a central region and two side regions on opposite sides of the central region, wherein the side regions are folded defining an overlapping region in a first state wherein the valve is at a first diameter and wherein the folded region is not folded in a second state wherein the valve is at a second diameter that is larger than the first diameter.

According to another example, ("Example 111"), a prosthetic valve, includes a first leaflet component and a second leaflet component being disposed downstream of and at least partially overlapping the first leaflet component defining an overlap region defining a width, the first leaflet component and the second leaflet component are in operable engagement configured to allow forward fluid flow through the prosthetic valve in a first direction extending downstream and prevent retrograde fluid flow through the prosthetic valve in an opposite direction extending upstream, and in operable engagement configured to allow the first leaflet and the second leaflet to slide relative to each other reducing the width of the overlap region as the diameter of the valve is increased.

According to another example, ("Example 112"), a prosthetic valve includes a diametrically adjustable frame comprising a plurality of frame elements coupled to a plurality of leaflets, each of the leaflets being secured to a respective one of the frame elements such that leaflet material is stored when the prosthetic valve is at a first diameter and each of the leaflets defines a first active size and is paid out to enlarge the active size of the each of the leaflets as the adjustable frame is diametrically enlarged.

According to another example, ("Example 113"), a prosthetic valve, includes a first diametrically adjustable frame element configured to support a valve structure and a second diametrically adjustable frame element coupled to the first diametrically adjustable frame element, the second diametrically adjustable frame element including a selective expansion feature for reinforcement of the first diametrically adjustable frame element against compression at a first diameter and reinforcement of the first diametrically adjustable frame element against compression following diametric expansion of the first frame element to a second diameter.

According to another example, ("Example 114"), further to Example 113, the selective expansion feature is configured to self-engage upon compression at the first diameter.

According to another example, ("Example 115"), further to Example 113, the selective expansion feature has an undulating shape at the first diameter and more straight, less undulating shape at the second diameter.

According to another example, ("Example 116"), a prosthetic valve includes a smaller, first prosthetic valve having a smaller inner diameter and including a first support structure and a first valve structure in an active state, a larger, second prosthetic valve having a larger inner diameter and including a second support structure and a second valve structure in an inactive state, the smaller, first prosthetic valve being releasably secured inside of the larger, second prosthetic valve such that the smaller, first prosthetic valve is configured to be retracted from the larger, second prosthetic valve and to transition the second valve structure to an active state.

According to another example, ("Example 117"), a method of treatment includes accessing a prosthetic valve according to any of the preceding Examples that has been implanted in a body of a patient and diametrically adjusting the prosthetic valve from a first inner diameter at which the prosthetic valve was implanted to a second, larger inner diameter.

According to another example, ("Example 118"), a method of forming a prosthetic valve that is diametrically adjustable includes manufacturing a prosthetic valve at an initial, maximum diameter with a valve structure of the prosthetic valve configured to coapt, and then diametrically compacting the prosthetic valve to a smaller inner diameter such that the inner diameter of the prosthetic valve is decreased and portions of a valve structure of the prosthetic valve are reversibly attached to an inner surface of the prosthetic valve, where portions of the valve structure that are unattached to the inner surface of the prosthetic valve are configured to operatively coapt at the smaller diameter.

According to another example, ("Example 119"), a method of treatment of a body conduit of a patient susceptible to changes in diameter over time includes delivering a prosthetic valve to a treatment site for the body conduit, the prosthetic valve including one or more primary leaflets and one or more auxiliary leaflets stored in an inactive state, and securing the prosthetic valve at the treatment site.

According to another example, ("Example 120"), further to the method of Example 119, further comprising diametrically adjusting the prosthetic valve implanted in a body of a patient from a first, active diameter to a second, larger, active diameter such that the one or more auxiliary leaflets release to an active state.

According to another example, ("Example 121"), a method of treatment of a body conduit of a patient susceptible to changes in diameter over time includes delivering a prosthetic valve to a treatment site for the body conduit, the prosthetic valve including one or more leaflets, wherein the leaflets define a contained portion and an uncontained portion that is exposed to a fluid flow through the valve when the valve defines a first diameter at which the prosthetic valve is configured to be implanted, the contained portion being releasable to become uncontained and exposed to a fluid flow through the valve upon expanding the prosthetic valve to a second diameter that is larger than the first diameter, and securing the prosthetic valve at the treatment site.

According to another example, ("Example 122"), further to the method of Example 121, the method also includes diametrically adjusting the prosthetic valve implanted in the patient from the first diameter to the second diameter such that the contained portion is released and exposed to a fluid flow through the valve.

According to another example, ("Example 123"), a method of treatment of a body conduit of a patient susceptible to changes in diameter over time includes delivering a prosthetic valve to a treatment site for a body conduit, the prosthetic valve including a support structure and a valve structure coupled to the support structure, the valve structure including, one or more primary leaflets, and one or more secondary leaflets adjacent to the primary leaflets, wherein the primary leaflets function to inhibit flow in a first direction and allow flow in a second direction through the prosthetic valve and the secondary leaflets are not functional to inhibit flow in the first direction and allow flow in the second direction through the prosthetic valve when the prosthetic valve is at the first, active diameter at which the prosthetic valve is implanted, and securing the prosthetic valve at the treatment site.

According to another example, ("Example 124"), further to the method of Example 123, the method also includes diametrically adjusting the prosthetic valve implanted in the patient from the first, active diameter to a second, larger, second active diameter such that the primary leaflets and the secondary leaflets function to inhibit flow in the first direction and allow flow in the second direction through the prosthetic valve after the prosthetic valve is transitioned to the second, larger active diameter.

According to another example, ("Example 125"), a method of treatment of a body conduit of a patient susceptible to changes in diameter over time includes delivering a prosthetic valve to a treatment site for a body conduit, the prosthetic valve including a support structure a valve structure coupled to the support structure, the valve structure including, one or more leaflets including a central region and two side regions on opposite sides of the central region, wherein the central region is configured to be active and the two side regions are configured to be inactive when the prosthetic valve is at the first diameter such that the valve structure operates to inhibit flow in a first direction and allow flow in a second direction through the prosthetic valve at the first diameter, and securing the prosthetic valve at the treatment site.

According to another example, ("Example 127"), further to the method of Example 125, the method also includes diametrically adjusting the prosthetic valve implanted in the patient from the first diameter to a second, larger diameter such that the central region and the two side regions are active at the second diameter and the valve structure operates to inhibit flow in the first direction and allow flow in the second direction through the prosthetic valve at the second, larger diameter.

According to another example, ("Example 128"), a method of treatment of a body conduit of a patient susceptible to changes in diameter over time includes delivering a prosthetic valve to a treatment site for a body conduit, the prosthetic valve including a support structure a valve structure coupled to the support structure, the valve structure including, one or more leaflets including a central region and two side regions on opposite sides of the central region, wherein the central region is releasably folded to define an overlapping region such that the valve structure operates to inhibit flow in a first direction and allow flow in a second direction through the prosthetic valve at a first diameter at which the prosthetic valve is implanted, and securing the prosthetic valve at the treatment site.

According to another example, ("Example 129"), The method of Example 128, the method also includes diametrically adjusting the prosthetic valve implanted in the patient from the first diameter to a second, larger diameter, the overlapping region of the central region is released and unfolded and the valve structure operates to inhibit flow in the first direction and allow flow in the second direction through the prosthetic valve at the second diameter.

According to another example, ("Example 130"), a method of treatment of a body conduit of a patient susceptible to changes in diameter over time includes delivering a prosthetic valve to a treatment site for a body conduit, the prosthetic valve, the prosthetic valve including a first leaflet component and a second leaflet component at least partially overlapping the first leaflet component to define an overlap region having a width, the first leaflet component and the second leaflet component being in operable engagement with one another at the first diameter at which the prosthetic valve is implanted to allow fluid flow through the prosthetic valve in a first direction and inhibit fluid flow through the prosthetic valve in an opposite, second direction and being configured to overlap to a lesser extent when the prosthetic valve is at a second diameter that is larger than the first diameter, and securing the prosthetic valve at the treatment site.

According to another example, ("Example 140"), further to the method of Example 130, the method also includes diametrically adjusting the prosthetic valve implanted in the patient from the first diameter to the second diameter such the first leaflet component and the second leaflet component remain in operable engagement with one another at the second diameter by sliding relative to each other thereby reducing the width of the overlap region as the diameter of the prosthetic valve is increased, such that the first and second leaflet components allow fluid flow through the prosthetic valve in the first direction and inhibit fluid flow through the prosthetic valve in the opposite, second direction at the second, larger diameter.

According to another example, ("Example 141"), a method of treatment of a body conduit of a patient susceptible to changes in diameter over time includes delivering a prosthetic valve to a treatment site for a body conduit, the prosthetic valve, the prosthetic valve including a diametrically adjustable frame comprising a plurality of frame elements slidably engaged with one another and a plurality of leaflets coupled to the diametrically adjustable frame, each of the leaflets being secured to a respective one of the frame elements such that stored leaflet material is stored in an inactive state when the adjustable frame is at the first diameter at which the prosthetic valve is implanted, each of the leaflets defining a first active size at the first diameter such that the leaflets allow fluid flow through the prosthetic valve in a first direction and inhibit fluid flow through the prosthetic valve in an opposite, second direction, and securing the prosthetic valve at the treatment site.

According to another example, ("Example 142"), further to the method of Example 141, the method also includes diametrically adjusting the prosthetic valve implanted in the patient from the first diameter to a second, larger diameter such that the plurality of frame elements slide relative to one another to diametrically enlarge the diametrically adjustable frame such that the stored leaflet material is paid out to enlarge the active size of the each of the leaflets to a second active size as the adjustable frame is diametrically enlarged to the second diameter, and such that each of the leaflets allow fluid flow through the prosthetic valve in the first direction and inhibit fluid flow through the prosthetic valve in the opposite, second direction at the second active size.

According to another example, ("Example 143"), a method of treatment of a body conduit of a patient susceptible to changes in diameter over time includes delivering a prosthetic valve to a treatment site for a body conduit, the prosthetic valve including a smaller, first prosthetic valve having a first inner diameter and including a first support structure and a first valve structure in an active state such that the first valve structure is configured to allow fluid flow through the prosthetic valve in a first direction and inhibit fluid flow through the prosthetic valve in an opposite, second direction and a larger, second prosthetic valve having a second inner diameter that is larger than the first inner diameter of the smaller, first prosthetic valve and including a second support structure and a second valve structure in an inactive state such that the second valve structure is inoperable to inhibit fluid flow through the prosthetic valve, wherein the smaller, first prosthetic valve is releasably secured within the larger, second prosthetic valve, and securing the prosthetic valve at the treatment site.

According to another example, ("Example 144"), further to the method of Example 143, the method also includes diametrically adjusting the prosthetic valve implanted in the patient from a first, active diameter to a second, larger, active diameter by releasing and removing the smaller, first prosthetic valve from the larger, second prosthetic valve to transition the second valve structure to an active state in which the second valve structure allows fluid flow through the prosthetic valve in the first direction and inhibits fluid flow through the prosthetic valve in the opposite, second direction.

According to another example, ("Example 145"), a method of treatment of a body conduit of a patient susceptible to changes in diameter over time includes delivering a prosthetic valve to a treatment site for a body conduit, the prosthetic valve having a first operative diameter including one or more primary leaflets of the prosthetic valve being operable to move between open and closed positions to allow and inhibit flow, respectively, through the prosthetic valve such that the primary leaflets are configured in an active state when the prosthetic valve is at the first operative diameter, the first operative diameter further including one or more auxiliary leaflets of the prosthetic valve being stored in an inactive state in which the auxiliary leaflets are inoperable to inhibit flow through the valve, and securing the prosthetic valve at the treatment site.

According to another example, ("Example 146"), further to the method of Example 145, the method also includes diametrically adjusting the prosthetic valve implanted in the patient to a second operative diameter including the one or more auxiliary leaflets being transitioned from the inactive state to an active state in which the one or more auxiliary leaflets are operable to move between open and closed positions to allow and inhibit flow, respectively, through the prosthetic valve.

The foregoing Examples are just that, and should not be read to limit or otherwise narrow the scope of any of the inventive concepts addressed herein.

BRIEF DESCRIPTION OF THE DRAWINGS

The accompanying drawings are included to provide a further understanding of the disclosure and are incorporated in and constitute a part of this specification, illustrate embodiments, and together with the description serve to explain various inventive concepts addressed herein.

FIGS. 21-23 illustrate additional or alternative expansion features for the prosthetic valve, according to some embodiments.

FIGS. 28-30 illustrate additional or alternative expansion features for the prosthetic valve, according to some embodiments.

FIGS. 31-34 illustrate additional or alternative expansion features for the prosthetic valve, according to some embodiments.

FIGS. 36-42 illustrate a diametrically expandable prosthetic valve, according to some embodiments.

FIGS. 43-45 illustrate retaining features according to some embodiments.

Figures 1, 2:
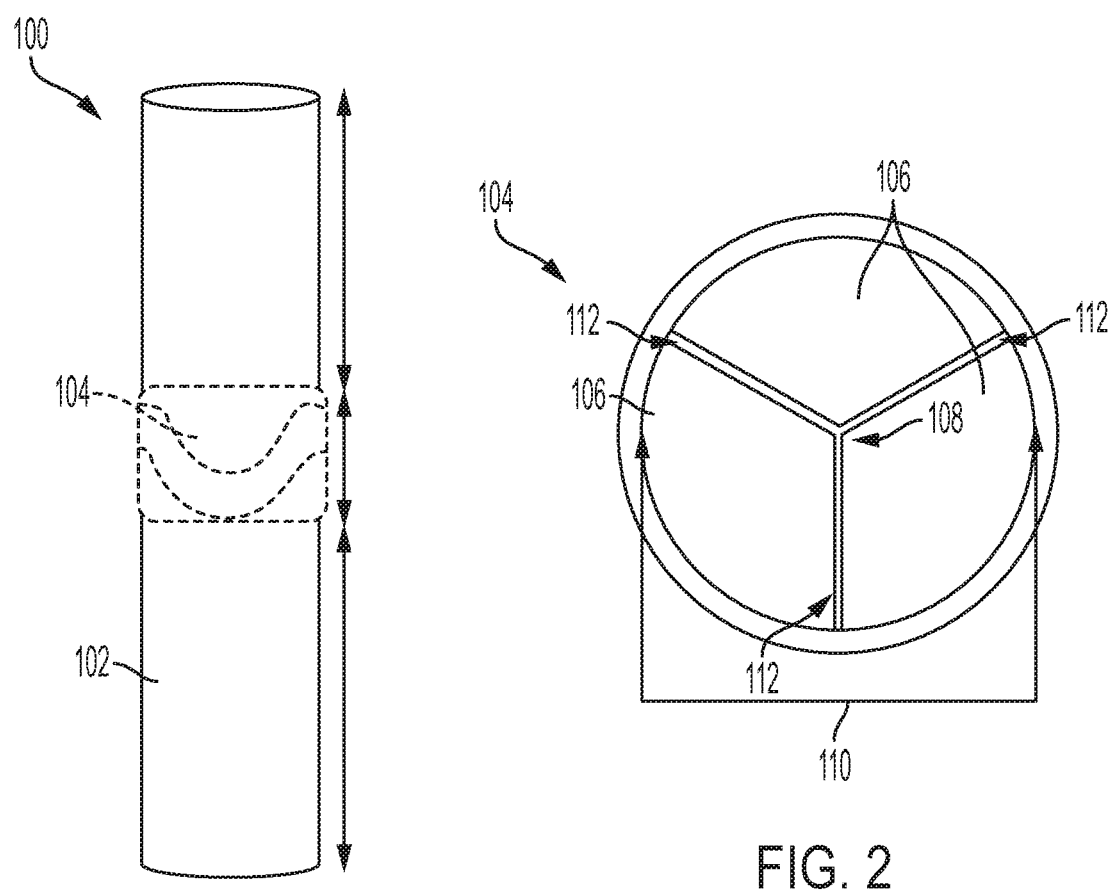
FIG. 1 illustrates features of a diametrically adjustable prosthetic valve, according to some embodiments.
FIG. 2 illustrates an interior downstream view of a valve structure of the prosthetic valve of FIG. 1, according to some embodiments.

Persons skilled in the art will readily appreciate that various inventive aspects described herein can be realized by any number of methods and apparatus configured to perform the intended functions. It should also be noted that the accompanying drawing figures referred to herein are not necessarily drawn to scale, but may be exaggerated to illustrate various inventive aspects, and in that regard, the drawing figures should not be construed as limiting.

DETAILED DESCRIPTION

Various features and associated advantages are described for diametrically adjustable support structures, adjustable valve structures, removable/replaceable valve structures, and associated systems and methods. Various examples of prosthetic valves suitable for implantation in a body conduit of a patient (e.g., a natural heart valve orifice, pulmonary artery, or aortic artery) that is susceptible to changes in diameter over time (e.g., as a result of patient growth, degenerative conditions such as an enlarged heart, or other causes). Although some examples are directed toward prosthetic valve that is a conduit having a valve structure, or a "valved conduit" (e.g., used to replace a pulmonary valve and a portion of the corresponding pulmonary artery or an aortic valve and the aortic root), and other examples are directed toward prosthetic valves implanted in native valve orifices (e.g., to replace an aortic or mitral valve), the features and advantages of the structures associated with those examples are interchangeable regardless of a particular application for which the examples are described.

In each of the described embodiments, it is contemplated that the various diametric adjustment features of the embodiments facilitate a change (increase) in diameter from a first active state at a first diameter to another active state at a second, larger diameter, wherein the increase in diameter of a desired amount. For example, it is expressly contemplated that the various diametric adjustment features for each of the embodiments may achieve a change in diameter between first and second active, or operative diameters of at least 10%, at least 20%, at least 30%, at least 50%, at least 100%, at least 200% or more as well as any and all ranges and values between each of the foregoing values (e.g., 15% or between 10% and 200%). These values are provided as examples only, and designs configured to achieve smaller or greater diametric adjustability are also contemplated.

Although the embodiments addressed herein may be described in connection with various principles and beliefs, the described embodiments should not be bound by theory. For example, various examples are described in connection with prosthetic valves used in cardiac applications, although the features and concepts of this disclosure can be applied toward any prosthetic valve of similar structure and/or function, including non-cardiac applications.

Terminology and Definitions

As the terms are used herein with respect to ranges of measurements "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like. In the event it is determined that individuals having ordinary skill in the relevant arts would not readily ascertain values for such reasonably small differences, the terms "about" and "approximately" can be understood to mean plus or minus 10% of the stated value.

Certain terminology is used herein for convenience only. For example, words such as "top", "bottom", "upper," "lower," "left," "right," "horizontal," "vertical," "upward," and "downward" merely describe the configuration shown in the figures or the orientation of a part in the installed position. Indeed, the referenced components may be oriented in any direction. Similarly, throughout this disclosure, where a process or method is shown or described, the method may be performed in any order or simultaneously, unless it is clear from the context that the method depends on certain actions being performed first. Various terms may be called out in a manner that indicates they may be used interchangeably in the following description. For example, the terms "auxiliary leaflet" and "secondary leaflet" are used interchangeably.

Description of Various Embodiments

FIG. 1 shows a prosthetic valve 100, also described as a valved conduit 100, according to some examples. The prosthetic valve 100 includes a support structure 102 (optionally described as a conduit 102 according to some examples) with a valve structure 104 (indicated generally by a box in broken lines) arranged within the support structure 102. The support structure 102 may include an upstream end (also described as an inflow end) and a downstream end (also described as an outflow end) and the valve structure 104 may be configured to allow flow in one direction through the prosthetic valve 100 (e.g., from the upstream end to the downstream end) while inhibiting or preventing flow in an opposite direction (e.g., from the downstream end to the upstream end).

The prosthetic valve 100 may be used, in a non-limiting example, as a shunt for connecting the right ventricle to the pulmonary artery following a Norwood operation, as frequently performed for the treatment of hypoplastic left heart syndrome (HLHS). In some examples, the prosthetic valve 100 is indicated for the correction or reconstruction of the right ventricle outflow tract (RVOT) in pediatric patients or application in any of a variety of heart disorders. For example, the prosthetic valve 100 may be utilized in other areas of the heart (e.g., in repair or replacement of the native aortic or mitral valves) or even other areas of the body (e.g., in the venous system, the biliary system, or elsewhere in the body).

In various examples, the support structure 102 is tubular in shape and configured as a conduit for bodily fluids (e.g., blood). The support structure 102 may include a graft or similar tubular conduit, a frame or similar construct (e.g., a stent), or combinations thereof. The support structure 102 may be diametrically expandable (e.g., self-expanding or expandable upon application of a radial expansion force).

FIG. 2 illustrates an interior downstream view of the valve structure 104 in a closed configuration. The valve structure 104 includes one or more leaflets 106 that extend into an interior of the support structure 102. Although three leaflets 106 are shown in FIG. 2, the valve structure 104 may include one, two, four, five, six, seven, eight or any number of leaflets 106. As shown in FIG. 2, the leaflets 106 close toward a center 108 of the support structure 102 when in the closed configuration. In an open configuration, fluid may flow through the valve structure 104 with the leaflets 106 being forced toward an inner surface 110 of the support structure 102. Generally, the valve structure 104 is coupled to and/or extends from the inner surface 110 of the support structure 102.

The leaflets 106 are coupled or attached to the support structure 102 to define the valve structure 104. The term "coupled," as used herein, means joined, connected, attached, adhered, affixed, or bonded. In examples using adhesion, the leaflet(s) 106 are adhered to an interior and/or exterior surface of the support structure 102 by an adhesive, thermal bonding, or chemical bonding as desired. Regardless, some portion of each leaflet 106 is coupled to the support structure 102. As shown in FIG. 2 gaps 112 may be provided between each of the leaflets 106 if desired, which can help allow some limited backflow through the valve structure 104. Such backflow may lessen the opportunity for blood to stagnate behind the leaflets 106, which may otherwise lead to thrombus formation. In cardiac applications, such as pulmonary valve conduit replacement, the gaps 112 can be sized such that leakage resulting from the backflow is minimal and does not otherwise increase strain on the patient's heart to pump blood through the prosthetic valve 100. In some examples, the prosthetic valve 100 does not include gaps 112 at a first inner diameter, and then, following diametric expansion, the gaps 112 existing between the leaflets 106 at a second, larger inner diameter as a result of the expansion. In a related aspect, in some examples, the gaps 112 exist at a first width at the first inner diameter and are enlarged as a part of diametric expansion of the prosthetic valve 100 to the second inner diameter. Thought the gaps 112 are shown extending to the center 108, in operation the gaps 112 may close along much of the leaflet edges and remain open near the leaflet perimeters adjacent the inner surface 110 of the support structure 102.

Figure 3:
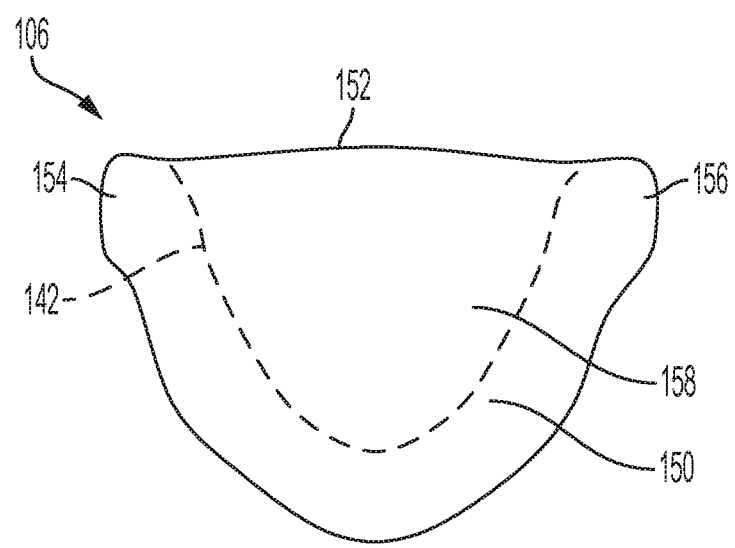
FIG. 3 is an illustration of a leaflet that may be used in the valve structure of FIG. 2, according to some embodiments.

FIG. 3 is a schematic view of a first one of the leaflet(s) 106. As shown, the leaflet 106 has an attachment zone 142 around a perimeter of the leaflet 106 corresponding to a portion of the leaflet 106 coupled to the support structure 102. Although the attachment zone 142 is shown as a continuous area around the perimeter of the one or more leaflets 106, the attachment zone 142 may include one or more discontinuous areas (e.g., formed of one or more separate tabs of material).

Each of the leaflets 106 may be coupled to the inner and/or outer surface of the support structure 102 as desired. For example, the support structure 102 may include one or more openings (e.g., slots) through which portions of the leaflets 106, such as the attachment zone 142, may pass. Additionally, or alternatively, the attachment zone 142 may be coupled to the inner surface of the support structure 102 (e.g., using adhesives, thermal bonding, or other coupling mechanism). Regardless, the attachment zone 142 generally corresponds to a portion of the leaflet 106 that is coupled to the support structure 102 according to various examples.

The remaining portion of each of the leaflets 106 defines a base 150 of the leaflet 106, a free edge 152 of the leaflet 106, a first commissure region 154, a second commissure region 156 and a belly region 158. As shown in FIG. 2, each of the leaflets 106 extends into the support structure 102 and toward the center 108 of the support structure 102. As will be described in greater detail, each of the one or more leaflets 106 can be sized, shaped, and otherwise configured to permit some diametric expansion of the support structure 102 while maintaining proper functioning of the valve structure 104.

Figure 4:
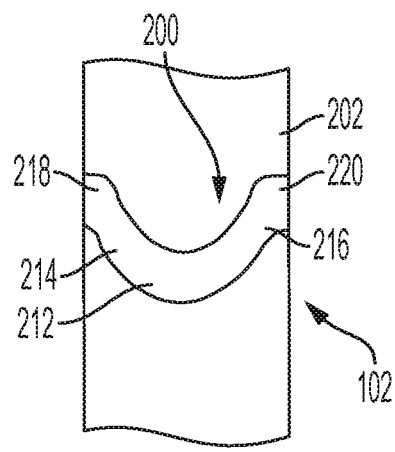
FIG. 4 shows an area of the support structure of a prosthetic valve corresponding to a valve structure of the prosthetic valve, according to some embodiments.

FIG. 4 shows an area of the support structure 102 proximate the location of the valve structure 104 (FIG. 3). In certain examples, the support structure 102 may be formed of materials including expanded polytetrafluoroethylene (ePTFE), although a variety of materials are contemplated. Though not separately shown in FIG. 4, in some examples, the support structure 102 includes a frame (e.g., such as those subsequently described, including those described in association with FIGS. 36-49). As described below, the support structure 102 (or portions thereof) is optionally diametrically adjustable. In some examples, the prosthetic valve 100, including the support structure 102, is diametrically expandable over time under physiologic conditions (e.g., by a creep mechanism) and in some examples is diametrically expandable by application of a sufficient radial expansion force (e.g., during a transcatheter expansion procedure). Combinations of both natural, physiologic diametric expansion mechanisms and applied, or manual diametric expansion mechanisms are also contemplated.

As described below, one or more regions of the support structure 102 and/or the valve structure 104 may be configured to exhibit expansion over a greater period of time (e.g., via a creep mechanism) that may span days, months, or years (e.g., so that the prosthetic valve 100 adjusts diametrically in a manner that correlates to a desired portion of a growth curve of a patient). For reference, in any of the examples where expansion over time is desired via creep mechanism, materials forming portions of the prosthetic valve 100 may be naturally susceptible to creep (e.g., made of a material that is less resistant to creep over a particular pressure range) or made susceptible to creep by various techniques (e.g., by lasing, perforating, plasma treating, etching, heat treating or otherwise modifying the physical characteristics of the deformation regions 252).

In the case where deformation upon application of a sufficient force is desired, materials forming portions of the prosthetic valve 100 may be made frangible and/or plastically deformable by various techniques. For example, materials forming portions of the prosthetic valve 100 may include a coating, reinforcement layer, or other feature that factures, deforms, or otherwise releases once sufficient expansion force is applied. Articles made of a porous material (e.g., ePTFE) having a fibrillar microstructure of bent fibrils may be provided with a fracturable coating (e.g., FEP) whereby the physical size (e.g., circumferential aspect) of the prosthetic valve 100 may be enlarged upon application of force in a direction substantially parallel to a direction of orientation of the fibrils (e.g., an expansion force resulting in a tensile force in the material in a circumferential direction). Such tensile force can result in fracturing of the fracturable material, straightening of the bent fibrils, and a concomitant non-recoverable diametric adjustment. Non-exclusive examples of such suitable materials and coatings can be found in U.S. Pat. No. 9,522,072 to Kovach et al., filed by W.L. Gore & Associates, Inc. on Mar. 6, 2014.

As shown in FIG. 4, the support structure 102 includes a support portion 200 and an optional conduit portion 202. In various examples, one or more sections of the conduit portion 202 are formed to be diametrically adjustable (e.g., over time and/or upon application of an expansion force, as previously referenced). Diametric adjustment features can include folds, or corrugations (see, e.g., description of longitudinal folds), materials or arrangements that are diametrically adjustable upon imparting sufficient expansion force (see, e.g., description of coatings, reinforcement layers, and/or other features that release once sufficient expansion force is applied), and/or materials or arrangements that account for diametric adjustment over time (see, e.g., description of creep mechanisms), or any of a variety of other diametric adjustment features as desired.

In various examples, the support portion 200 of the support structure 102 corresponds to the location where the valve structure 104 is coupled to the support structure 102. Although the support portion 200 is shown with an outline corresponding to the shape of the attachment zone 142, it should be understood that this is a non-limiting example, and the support portion 200 may have alternative shapes as desired.

In FIG. 4, the support portion 200 is shown to have the general shape of the attachment zone 142 of the leaflets 106 (e.g., as the attachment zone 142 would appear superimposed on the support structure 102). As shown, the support portion 200 optionally defines an arcuate or U-shape, with a base 212, a first leg 214, a second leg 216, a first commissure support 218, and a second commissure support 220. For reference, the first commissure support 218 and the second commissure support 220 operate and function as commissure posts and as such that "post" nomenclature may be used interchangeably for the first commissure support 218 and the second commissure support 220.

In some examples, the support portion 200 is configured to assist with supporting the valve structure 104 under physiologic conditions and to resist deformation under expansion forces imparted on the support portion 200 (e.g., radial expansion forces from a balloon catheter or physiologic forces from blood pressure). In some examples, the support portion 200 (or regions thereof) includes materials that are densified, rigidified, or otherwise treated or structured to increase resistance to instantaneous and/or chronic deformation during operating conditions, as well as during diametric expansion of the conduit portion 202. For reference, densification refers to a process of selectively making a material more dense at desired locations, such as by heating and/or pressure. For example, in certain embodiments, the support structure 102 is formed from ePTFE that is densified in one or more areas to reduce porosity and make the areas more rigid.

If desired, one or more layers, coatings, and/or surface treatments may be applied to the support portion 200 to selectively enhance resistance to deformation. For example, fluorinated ethylene propylene (FEP), polyether ether ketone (PEEK), and/or other material may be applied to the support portion 200 to add selective resistance to deformation to the support portion 200. As still another additional or alternative option, the support portion 200 may include one or more reinforcement elements (e.g., a continuous or discontinuous fiber, strand, bead, wire, or other reinforcement element) to help provide selective resistance to deformation.

Figure 5:
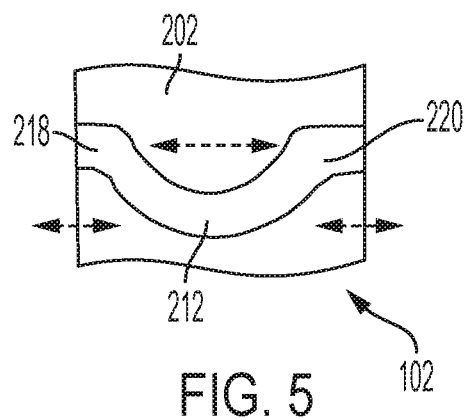
FIGS. 5-7 show various support portion features, according to some embodiments.

Regardless of the deformation mechanism (instantaneous or chronic), as indicated in FIG. 5 by the broken line arrows, in some examples diametric expansion of the conduit portion 202 adjacent the support portion 200 occurs while one or more areas of the support portion 200 resist deformation and maintain valve structure 104 operability. This resistance to deformation can help the support portion 200 maintain a more consistent dimension with the attachment zones 142 (FIG. 3) while still allowing diametric expansion of the support structure 102. In some examples, the valve structure 104, and in particular the geometries of the one or more leaflets 106 are selected to accommodate this diametric expansion. For example, the leaflets 106 may include additional material in the belly region of the leaflets 106 to accommodate a reduction in overall height of the valve structure 104 that may occur as the inner diameter of the support structure 102 and the diameter of the valve structure 104 increases.

Figure 6:
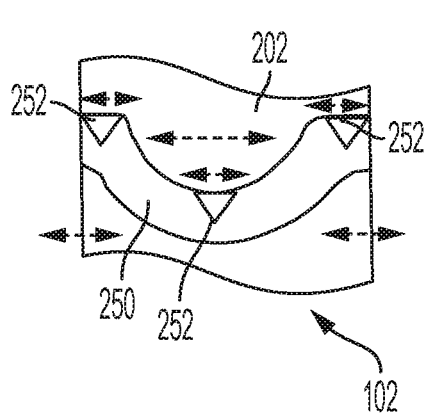
Figure 7:
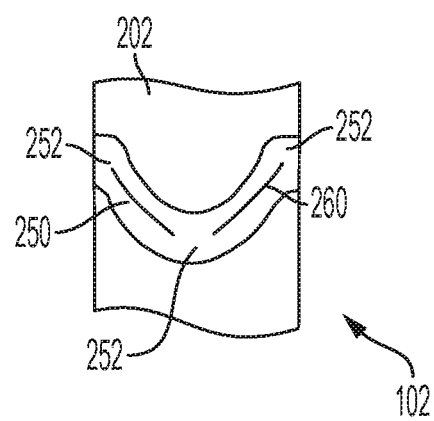

In some examples, one or more regions of the support portion 200 exhibit a desired amount of expansibility (e.g., over time under physiologic loading and/or upon application of a sufficient force). These regions may act as hinges or expansion zones. In different terms, the support portion 200 may be configured to selectively deform, or deform to a greater extent in some regions than others. As shown in FIGS. 6 and 7, for example, the support portion 200 optionally includes one or more resistant regions 250 and one or more deformation regions 252, or yield regions, where the resistant regions 250 have relatively increased resistance to deformation and the deformation regions 252 have relatively decreased resistance to deformation so that preferential expansion during diametric adjustment of the support portion 200 occurs at the deformation regions 252.

Concomitant deformation of the support portion 200 may result in a change in the saddle or U-shaped design previously-described, such as the first commissure support 218 and the second commissure support 220 separating, or moving away from one another, the first leg 214 and the second leg 216 separating, or moving away from one another, and the base 212 widening with the overall U-shape of the support portion 200 becoming more shallow. This widening and shallowing of the support portion 200 may translate to the valve structure 104 or the valve structure may similarly include decreased resistance to deformation at those areas to match the support portion 200. Generally, the leaflets 106 may be configured to better accommodate the diametric increase and any associated geometric shift of the support portion 200 (e.g., by including additional material in the belly region of the leaflets 106) and/or including expansion/diametric adjustment features such as those described in association with various examples in this disclosure.

If desired, one or more layers, coatings, and/or surface treatments may be applied to the support portion 200 at the resistant regions 250 that enhance resistance to deformation at the resistant regions 250. The one or more layers, coatings, and/or surface treatments may be left from and not applied to the deformation regions 252 to encourage preferential deformation at the deformation regions 252 relative to the resistant regions 250. For example, fluorinated ethylene propylene (FEP), polyether ether ketone (PEEK), and/or other material may be applied to the resistant regions 250 and left from the deformation regions 252 (and the areas of the conduit 202 around the support portion 200) to add selective resistance to deformation to the support portion 200.

As still another additional or alternative option, as shown in FIG. 7, the resistant regions 250 may include one or more reinforcement elements 260 (e.g., a continuous or discontinuous fiber, strand, bead, wire, or other reinforcement element) that helps provide selective resistance to deformation.

Regardless, the deformation regions 252 (and/or the areas of the conduit 202 around the support portion 200) can be configured to be more susceptible to deformation (e.g., under a diametric expansion force applied to the support portion 200) than the resistant regions 210. In some examples, the deformation regions 252 are more susceptible to creep under physiologic conditions (e.g., to permit selective diametric expansion over time) than the resistant regions 210. Additionally or alternatively, the deformation regions 252 may be susceptible to deformation upon application of a sufficient expansion force (e.g., to permit deformation by catheter balloon expansion) while being resistant to creep. The deformation regions 220 may be made more susceptible to creep in any of the manners previously described or configured to permit deformation upon application of a sufficient force in any of the manners previously described.

As referenced above, in certain embodiments, the prosthetic valve 100 may additionally or alternatively include a support frame (not shown) at the support portion 200 (e.g., to help prevent unwanted or irregular compression/deformation at the valve structure 104). Such support frames can also be configured to support diametric adjustment of the prosthetic valve 100, as subsequently described in various examples.

Figure 8:
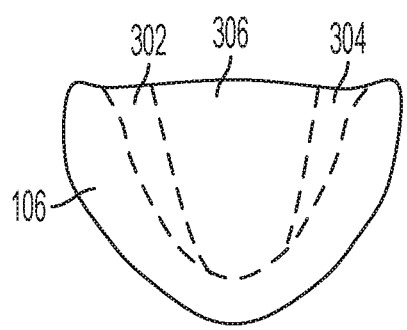
FIG. 8 shows a leaflet with various regions thereof outlined in broken lines, according to some embodiments.

Additionally or alternatively to the aforementioned features of the support structure 102, each of the leaflets 106 may include one or more expansion features to accommodate expansion of the prosthetic valve 100, and in particular diametric expansion of the prosthetic valve 100 at the valve structure 104 and/or the support portion 200. As shown in FIG. 8, the leaflet 106 includes a first side region 302, a second side region 304, and a central region 306 in the operative region, or belly region 158.

Although a variety of materials are contemplated, each of the leaflets 106 may include a composite material comprising an expanded fluoropolymer membrane (e.g., ePTFE) and an elastomer or elastomeric material. It should be appreciated that multiple types of fluoropolymer membranes and multiple types of elastomer or elastomeric materials can be combined to form a suitable composite material. Additional or alternative suitable biocompatible polymers include, but are not limited to, urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

In some examples, each of the leaflets 106 is configured to account for some of the change in shape of the support portion 200 so that the valve structure 104 still properly functions over multiple inner diameters as the support portion 200 is deformed. For example, the belly region 158 of each of the leaflets 106 may be relatively deeper (e.g., bend further inwardly into the valve) prior to diametric expansion, with the belly region 158 becoming more shallow to account for diametric expansion and the change in shape of the support portion 200 (e.g., as shown in FIG. 5). Thus, the leaflets 106 can have geometry that is pre-selected to accommodate diametric expansion (including the ability to accommodate a somewhat elongated geometry at a smaller diameter and a shallower belly geometry at a larger diameter). Stated differently, the geometry of the leaflets 106 may be predetermined to allow leaflet deformation to accommodate the increase in diameter.

Additionally or alternatively, the overall geometry of the valve structure 104 can be changed or adjusted during expansion of the prosthetic valve 100, such that as the inner diameter of the prosthetic valve 100 increases and thus the diameter of the valve structure 104 increases, each of the leaflets 106 accommodates the change in diameter by increasing in operative size. In particular, the leaflets 106 may have one or more portions (contained, inoperable, or inactive portions) that are expansible, adjustable, or deployable from a stored condition (contained, inoperable, or inactive state) to a released condition (exposed, operable, or active state) to accommodate diametric expansion of the valve structure 104.

In some examples, one or more of the first side region 302, the second side region 304, and the central region 305 (including portions thereof) are releasably secured to the support structure 102 such that the leaflet 106 has a first geometry (e.g., the actuating portion of the leaflet 106 has a first size/shape) suitable for operation of the valve structure 104 at a first inner diameter and upon release from the support structure 102 during diametric enlargement of the prosthetic valve 100 the leaflet 106 takes on a second geometry (e.g., the actuating portion of the leaflet 106 has a second, larger size/shape) suitable for operation of the valve structure 104 at a second, larger inner diameter.

As non-liming examples, the first side region 302, the second side region 304, and/or the central region 306 (or portions thereof) may be releasably secured to the support structure by any of a variety of means, including a fracturable coating or adhesive, a biodegradeable adhesive, a breakable fastener (e.g., a suture), a biodegradeable fastener (e.g., a suture), or by other means such that the secured portion(s) are freed upon imparting a sufficient expansion force on the prosthetic valve 100 and/or after sufficient time passes for biodegradable features to biodegrade.

Figure 9:
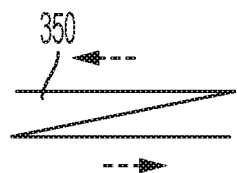
FIGS. 9 and 10 represent expansion features for the prosthetic valve, according to some embodiments.

In some examples, one or more of the first side region 302, the second side region 304, and the central region 306 (or portions thereof) include one or more folds 350 (shown generally in FIG. 9), or corrugations, that are secured together (e.g., by a fracturable coating, a biodegradeable adhesive, a breakable fastener, a biodegradeable fastener, or other means) such that the folds are freed upon imparting a sufficient expansion force on the prosthetic valve 100 and/or after sufficient time passes for biodegradable features to biodegrade. Again, the folds 350 can facilitate the leaflet 106 transitioning from a first geometry (e.g., the actuating portion of the leaflet 106 has a first size/shape) configured for operation of the valve structure 104 at a first inner diameter and upon release of the one or more folds 350, the leaflet 106 takes on a second geometry (e.g., the actuating portion of the leaflet 106 has a second, larger size/shape) configured for operation of the valve structure 104 at a second, larger inner diameter.

Figure 10:
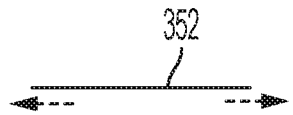

In some examples, one or more of the first side region 302, the second side region 304, and the central region 306 (or portions thereof) include an expansible material 352 (shown generally in FIG. 10), such as one of the material arrangements previously described that are configured to facilitate creep over time or expansion upon exceeding a requisite expansion force. Again, the expansible material can facilitate the leaflet 106 transitioning from a first geometry configured for operation of the valve structure 104 at a first inner diameter and upon expansion of the expansible material 352, the leaflet 106 takes on a second (e.g., larger) geometry suitable for operation of the valve structure 104 at a second, larger inner diameter.

Figure 11:
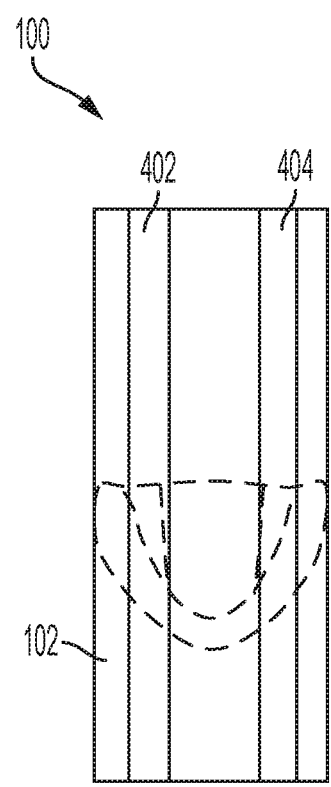
FIGS. 11-13 illustrate expansion features for the prosthetic valve, according to some embodiments.
Figure 12:
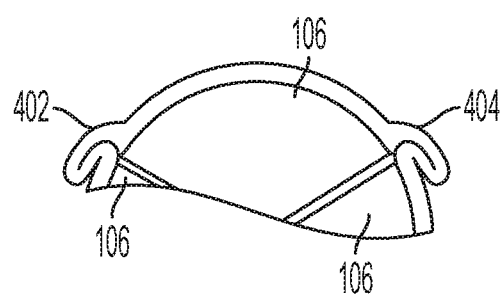
Figure 13:
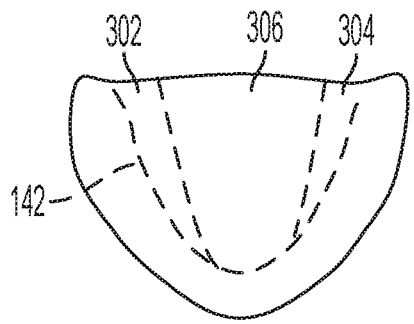

FIGS. 11-13 show additional or alternative diametric expansion features for the prosthetic valve 100. As shown, the support structure 102 includes one or more longitudinal folds, such as a first longitudinal fold 402 and a second longitudinal fold 404 that are releasable to permit diametric expansion of the prosthetic valve 100. Longitudinal folds may be incorporated at the areas corresponding to each of the commissure regions of the valve structure 104 as desired. Such longitudinal folds are releasably secured together by any of a variety of means, including using a fracturable coating, a biodegradeable adhesive, a breakable fastener (e.g., a suture), a biodegradeable fastener (e.g., a suture) or other means such that the folds are freed upon imparting a sufficient expansion force on the prosthetic valve 100 and/or after sufficient time passes for biodegradable features to biodegrade.

In some examples, the first side region 302 is secured within the first longitudinal fold 402 when the prosthetic valve 100 and in particular the valve structure 104 is at a first inner diameter (FIG. 12) and/or the second side region 304 is secured within the second longitudinal fold 404 when the prosthetic valve 100, and in particular the valve structure 104, is at the first inner diameter. Upon release of the first longitudinal fold 402 and the second longitudinal fold 404, the prosthetic valve 100 and in particular the valve structure 104 increases to a second, larger inner diameter (not shown), where the first side region 302 and the second side region 304 of the leaflet 106 are made available and the operative shape, or geometry, of the leaflet 106 is increased to account for the increase in inner diameter.

Some examples include the ability to increase leaflet size by storing portions of the leaflet 106 in folds, such as the first longitudinal fold 402 and the second longitudinal 404. Such longitudinal folds may also be employed for facilitating expansion of the support portion 102 while other features are incorporated for the valve structure 104 to account in the diametric change, including any of those features previously described for the support portion 200. For example, the leaflets 106 may include folds, such as folds 350 or expansible material, such as expansible material 352, independently from the support portion 102 that are releasable to account for diametric expansion of the prosthetic valve 100. Stated differently, it is contemplated that the various expansion features referenced for the leaflets 106 may be employed for the support structure 102, and vice versa.

Figure 14:
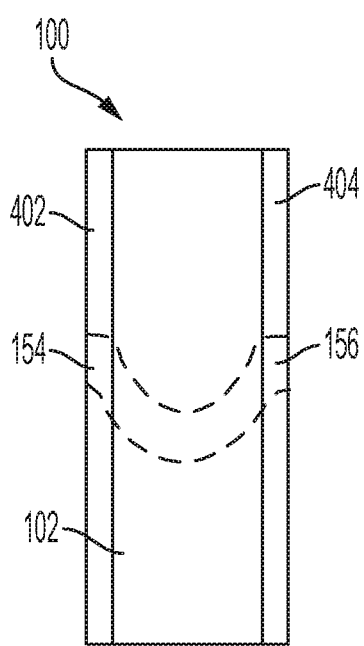
FIGS. 14-16 illustrate additional or alternative expansion features for the prosthetic valve, according to some embodiments.
Figure 15:
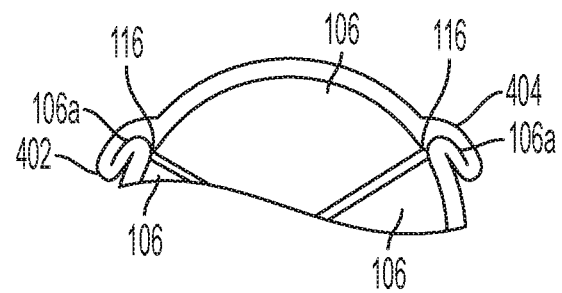
Figure 16:
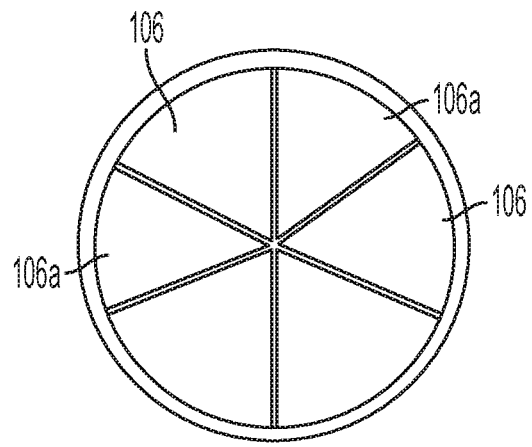

FIGS. 14-16 show additional or alternative diametric expansion features for the prosthetic valve 100. As shown, the support structure 102 includes one or more longitudinal folds, such as the first longitudinal fold 402 and the second longitudinal fold 404 that are releasable to perm it diametric expansion of the prosthetic valve 100. Again, such longitudinal folds are releasably secured together by any of a variety of means, including any of those previously described.

According various examples, such as that of FIGS. 14-16, a leaflet storage concept may be applied to the prosthetic valve 100 with added, or auxiliary leaflets (also described as secondary leaflets) that are initially contained (stored, or hidden) in an inoperable or inactive state by the prosthetic valve 100 (e.g., within a fold or other appendage of the prosthetic valve 100) such that when the valve diameter is increased, the stored auxiliary leaflet(s) are released and added to the complement of original leaflets to an operable or active state. In various examples, the commissure region where two original leaflets attach provides a potential location for attachment and storage of such auxiliary leaflets. In some such examples, when the inner valve diameter is increased, the commissure region splits apart, and the auxiliary leaflet 106a is deployed between the original leaflets (interchangeably described as "primary leaflets") at the split-apart commissure region. Additional examples of such auxiliary leaflet possibilities include a bileaflet arrangement (i.e., two leaflets 106) with an auxiliary leaflet 106a within a fold that is released and exposed to transfer the prosthetic valve 100 from a two-leaflet valve to a three-leaflet valve upon diametric expansion.

As indicated in FIGS. 14-16, an auxiliary leaflet 106a (e.g., similar to the original, or primary leaflet(s) 106, or larger or smaller than the original, or primary leaflet(s) 106) can be stored within the first longitudinal fold 402 and/or another auxiliary leaflet 106a can be stored within the second longitudinal fold 404 when the prosthetic valve 100 and in particular the valve structure 104 is at a first inner diameter (FIG. 15). Though not shown, any number of folds and associated auxiliary leaflets are contemplated.

As shown, the first longitudinal fold 402 and the second longitudinal fold 404 are positioned at locations along the support portion 200 corresponding generally to commissure regions 116 between the leaflets 106. The auxiliary leaflet(s) 106a are attached at commissure regions 116 between the leaflets 106. Upon release of the first longitudinal fold 402 and the second longitudinal fold 404, the commissure regions 116 each split in two as the prosthetic valve 100 and in particular the valve structure 104 transitions to a larger, second inner diameter (FIG. 16). Upon splitting, of the commissure regions 116 and opening of the first longitudinal fold 402, the second longitudinal fold 404 and any other folds (e.g., a third fold, though not shown), the auxiliary leaflet(s) 106 are released and are made available to coapt with the leaflets 106 to form part of the valve structure 104 and account for the increased inner diameter.

If desired, similar arrangements (e.g., a longitudinal fold and stored auxiliary leaflet) can be supplied between each of the leaflets 106 to provide a desired amount of diametric adjustment capability. Thus, in the example of FIGS. 14-16, the number of leaflets 106 may effectively double as a part of diametric expansion. Similar principles may be applied to increase the effective number of leaflets as desired.

Although some examples include the ability to increase an operative inner diameter of the valve structure 104 by storing one or more auxiliary leaflets in the support structure 102, it should be understood that such longitudinal folds may be employed for diametric adjustment of the support structure 102 and the leaflets 106 may be configured to account for the diametric increase in any of the manners previously described. If desired, the leaflets 106 themselves may include folds (e.g., such as folds 350) in the first side region 302 and/or second side region 304 of each of the leaflets 106 to store one or more of the auxiliary leaflets 106a that can be released during diametric adjustment to account for the increase in diameter of the valve structure 104. In such examples, the effective number of leaflets is increased (e.g., doubled, tripled, etc.) when transitioning from the smaller valve diameter to the larger valve diameter.

FIGS. 17-20 show additional or alternative diametric expansion features for the prosthetic valve 100. As shown, the support structure 102 includes one or more longitudinal folds that are releasable to permit diametric expansion of the prosthetic valve 100, such as the first longitudinal fold 402 in the position shown in FIG. 17. Such longitudinal folds are releasably secured together by any of a variety of means, including any of those previously described. The prosthetic valve 100 optionally includes any number of folds, including a fold extending longitudinally along the support structure 102 at a location generally corresponding to a center of each of the leaflets 106.

In various examples, the central region 306 of the leaflet 106 is stored within the first longitudinal fold 402 when the prosthetic valve 100 and in particular the valve structure 104 is at a first inner diameter (FIG. 18) and the first side region 302 and the second side region 304 remain exposed inside the support structure 102 to form sub-leaflets 106b that are each smaller than overall geometry of the leaflet 106. Upon release of the first longitudinal fold 402, the prosthetic valve 100 and in particular the valve structure 104 transitions to a larger, second inner diameter (FIG. 20), where the central region 306 is released and the sub-leaflets 106b transition into the leaflet 106, which is larger, and includes the central region 306, to form part of the valve structure 104 and account for the increased inner diameter. If desired, similar arrangements (e.g., a longitudinal fold and stored auxiliary leaflet) can be supplied for each of the leaflets 106 to provide a desired amount of diametric adjustment capability. In such examples, the effective number of leaflets is reduced (e.g., halved) when transitioning from the smaller valve diameter to the larger valve diameter.

Figure 20:
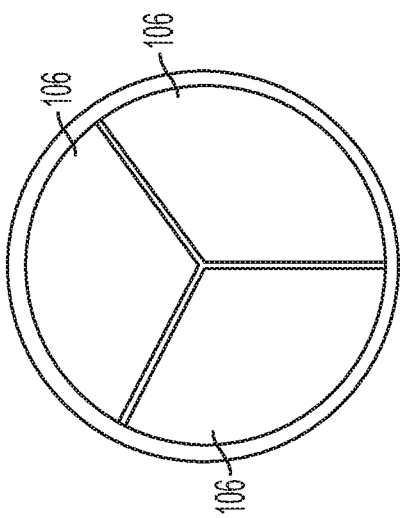
FIGS. 17-20 illustrate additional or alternative expansion features for the prosthetic valve, according to some embodiments.
Figure 18:
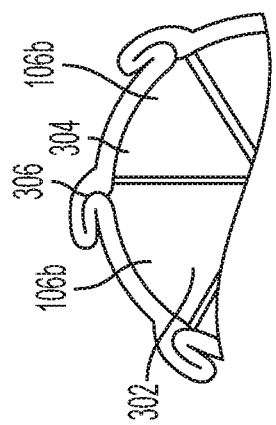
Figure 19:
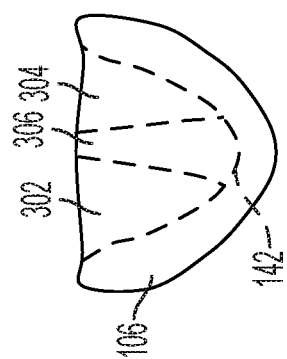
Figure 17:
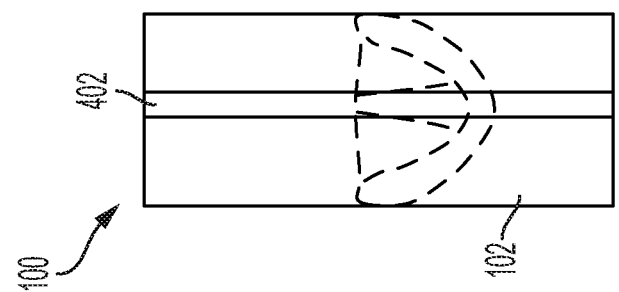

Although some examples include the ability to increase an operative inner diameter of the valve structure 104 by storing the central region(s) 306 of the leaflet(s) 106 in folds, such as the first longitudinal fold 402, it should be understood that such longitudinal folds may be employed for diametric adjustment of the support structure 102 and the leaflets 106 may be configured to account for the diametric increase in any of the manners previously described. If desired, the leaflets 106 themselves may include folds (e.g., such as folds 350) in the central region 306 of each of the leaflets 106 such that the leaflets 106 initially provide one or more sub-leaflets 106b and, upon release of the folds, release the central region 306 to fully form the leaflets 106 as shown in FIG. 20 to account for diametric adjustment.

FIGS. 21-23 show additional or alternative diametric expansion features for the prosthetic valve 100. In various examples, the prosthetic valve 100 is provided with an inflow and/or outflow portion that can increase in diameter as needed, while the support portion 200 and the valve structure 104 remain at a constant diameter. In certain instances, flow dynamics in a smaller conduit is desirable and, at some point in time, the flow dynamics of a larger conduit may be desirable.

As shown in FIGS. 21-23, the support portion 200 and the valve structure 104 are optionally formed at a larger inner diameter and one or more sections of the conduit portion 202 (e.g., inflow end portion 502 and/or outflow end portion 504) are formed at a smaller inner diameter and are diametrically adjustable as desired (upon exceeding a requisite diametric adjustment force and/or over time under physiologic conditions). Any of the features for facilitating diametric adjustment described herein (fracturable coatings, creep mechanisms, biodegradable features, folds, compression layers, etc.) are applicable for diametric adjustment of the inflow end portion 502 and/or outflow end portion 504.

Figure 24:
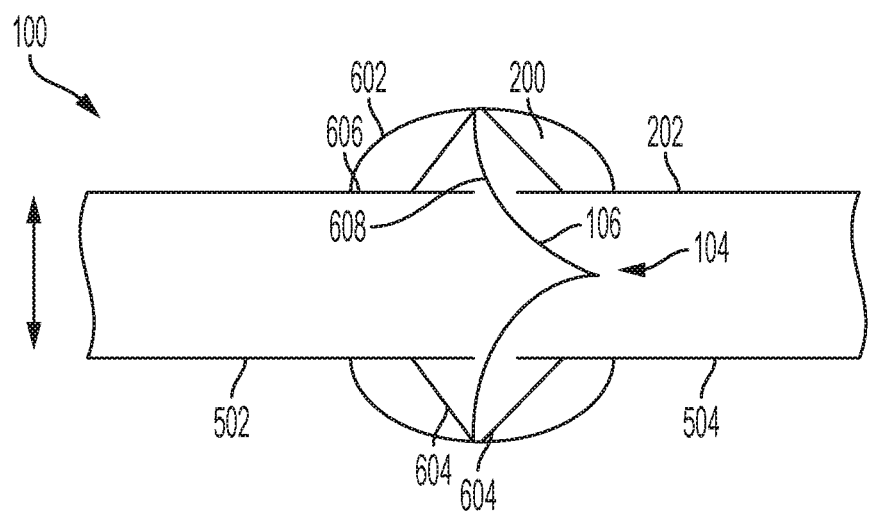
FIGS. 24-25 illustrate additional or alternative expansion features for the prosthetic valve, according to some embodiments.
Figure 25:
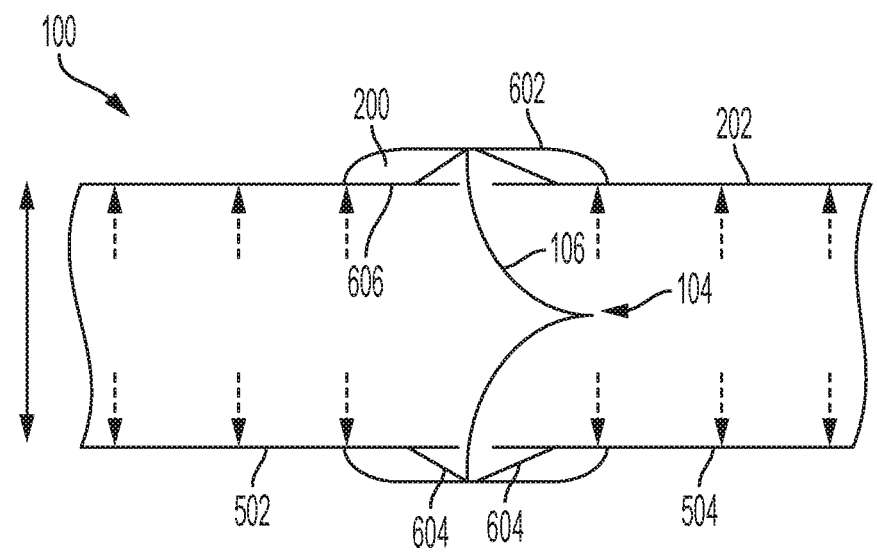

FIGS. 24-25 show additional or alternative diametric expansion features for the prosthetic valve 100. As shown in FIGS. 24-25, the support portion 200 includes a leaflet storage and release mechanism by which portions of the valve structure 104 are initially stored when the prosthetic valve 100 is at a first inner diameter (FIG. 24) and then made available as the prosthetic valve 100 is transitioned to a second, larger inner diameter (FIG. 25).

As shown, the support portion 200 includes an outer layer 602, a compression layer 604, and an inner layer 606. The support portion 200 is configured to retain and store one or more stored portions 608 of the one or more leaflets 106 between the outer layer 602 and the inner layer 606. In some examples, the leaflets 106 are secured to the outer layer 602 and/or the compression layer 604.

The inner layer 606 is capable of expanding outwardly against the compression layer 604, and the outer layer 602 optionally resists outward deformation such that the compression layer 604 is radially collapsed. The outward expansion of the inner layer 606 effectively increases the operating inner diameter of the prosthetic valve 100.

The compression layer 604 optionally includes one or more struts, biasing elements or other features that helps maintain spacing between the inner layer 606 and the outer layer 602. This spacing helps ensure that the stored portion 608 does not pull out during operation of the leaflets 106 when the prosthetic valve 100 is at the first inner diameter.

As the prosthetic valve 100 is transitioned to the second, larger inner diameter (FIG. 25) the compression layer 604 collapses and the stored portions 608 of the leaflets 106 are revealed or otherwise exposed to adjust the geometry of the one or more leaflets 106 to account for the change in inner diameter of the prosthetic valve 100. The stored portions 608 remain detached, or are detachable from the inner layer 606 during diametric expansion so that the stored portions 608 are able to be released from between the outer layer 602 and inner layer 606 to extend from the inner surface of the prosthetic valve 100 following diametric expansion of the prosthetic valve 100, and in particular during expansion of the inner diameter of the prosthetic valve 100.

Again, any of the features for facilitating diametric adjustment (fracturable coatings, creep mechanisms, biodegradable features, folds, compression layers, etc.) are applicable for diametric adjustment of the inner layer 606 and/or the conduit portion 202 to increase the effective inner diameter of the prosthetic valve 100.

Figure 26:
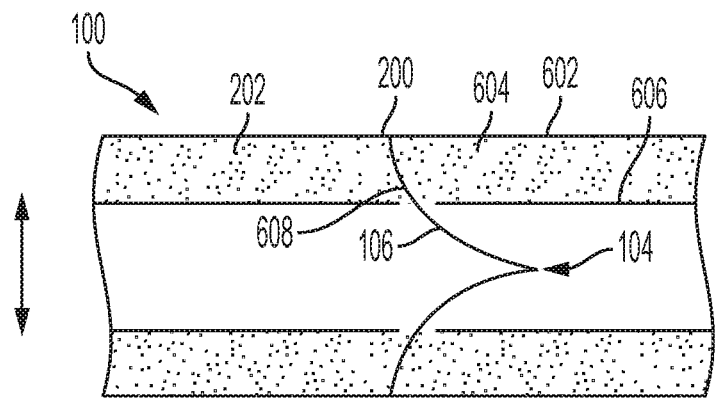
FIGS. 26-27 illustrate additional or alternative expansion features for the prosthetic valve, according to some embodiments.
Figure 27:
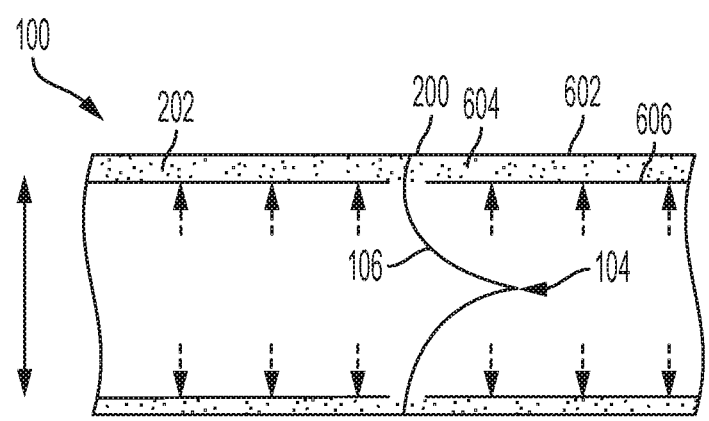

FIGS. 26-27 show additional or alternative diametric expansion features for the prosthetic valve 100. For example, as indicated in FIGS. 26-27, the compression layer 604 is optionally a layer of material that extends along a portion of the length of the prosthetic valve 100 (e.g., the entire, or the majority of the length). As previously referenced, the inner layer 606 and the outer layer 602 are optionally formed of any of the materials previously described for the support structure. Generally the outer layer 602 is resistant to distension or radial deformation, while the inner layer 606 is configured to be radially expanded (e.g., deformed). The compression layer 604 is optionally formed of a compressible material and/or otherwise defines a compressible space.

The inner layer 606 is again capable of expanding outwardly against the compression layer 604 while the outer layer 602 resists outward deformation such that the compression layer 604 is radially collapsed. Again, the outward expansion of the inner layer 606 effectively increases the operating inner diameter of the prosthetic valve 100.

In the example of FIGS. 26-27, the compression layer 604 can include a compressible material (e.g., foam or porous materials) and/or an incompressible material (e.g., liquid) that is expelled from the compression layer 604 (e.g., by diffusion and/or by being forced through the inner layer 606 and/or outer layer 602 under pressure). Similarly to the examples described in association with FIGS. 24-25, the compression layer 604 may include discrete mechanical elements (e.g., springs, struts, or other features) that are compressible under a radial expansion force on the prosthetic valve 100.

Again, in the example of FIGS. 26-27, the support portion 200 defines a leaflet storage and release mechanism by which stored portions 608 of the valve structure 104 are initially stored (e.g., between the outer layer 602 and the inner layer 606) when the prosthetic valve 100 is at a first inner diameter (FIG. 26) and then made available for adjusting the geometries of the one or more leaflets 10 as the prosthetic valve 100 is transitioned to a second, larger inner diameter (FIG. 27).

In some examples, the one or more leaflets 106 are secured to the outer layer 602 at the support portion 200. Initially, the prosthetic valve 100 is at a first inner diameter and, upon expansion of the inner layer 606 (e.g., by applying a radially outward expansion force to the inner layer 606), the compression layer 604 is compressed and the stored portions 608 of the leaflets 106 are revealed or otherwise made available to adjust leaflet geometry for operatively sealing the larger inner diameter. Generally, the stored portions 608 remain detached, or are detachable from the compression layer 604 and the inner layer 606 so that the stored portions 608 are able to be freed for actuation following diametric expansion of the inner diameter of the prosthetic valve 100.

Again, any of the features for facilitating diametric adjustment (fracturable coatings, creep mechanisms, biodegradable features, folds, compression layers, etc.) are applicable for diametric adjustment of the inner layer 606 and the support structure 102 in general.

FIGS. 28-30 show additional or alternative diametric expansion features for the prosthetic valve 100. Generally, the prosthetic valve 100 includes a first prosthetic valve 100a and a second prosthetic valve 100b, where the first prosthetic valve 100a is secured within the second prosthetic valve 100b. The second prosthetic valve 100b has larger inner diameter than the first prosthetic valve 100a such that the first prosthetic valve 100a can be nested inside the second prosthetic valve 100b. The smaller, first prosthetic valve 100a may be removed from the larger, second prosthetic valve 100b when needed. In some examples, removal may be facilitated by the ability to evert and peel the smaller, first prosthetic valve 100a from within the larger, second prosthetic valve 100b. Although an arrangement of two valve structures is shown and described, it should be understood that any number of prosthetic valves (three, four, six, etc.) may be employed as desired.

The first prosthetic valve 100a defines an inner diameter and includes a support structure 102a and a valve structure 104a operatively coupled to the support structure 102a. Prior to removal of the first prosthetic valve 100a, the valve structure 104a is in an active state. The first prosthetic valve 100a optionally includes similar features and functions as the prosthetic valve 100, including any of the previously-described support and valve structures.

The second prosthetic valve 100b also includes a support structure 102b and a valve structure 104b which may include features similar to those of any of the previously-described support structures and valve structures. As shown, the second prosthetic valve 100b includes a support layer 702b which may be coupled to the valve structure 104b and an intermediate layer 704a disposed inside of the support layer 702b. Prior to removal of the first prosthetic valve 100a, the valve structure 104b is in an inactive state, according to some examples.

In some examples, the intermediate layer 704a is releasably coupled to the support structure 102a of the first prosthetic valve 100a. The support structure 102a optionally includes one or more release features (not shown), such as tabs, perforations, fibers, or other means for exerting a tension force on the support structure 102a to release and remove the first prosthetic valve 100a from the interior of the second prosthetic valve 100b. As previously referenced, the support structure 102a is optionally retracted and everted as indicated by the curved, broken arrows in FIG. 28, resulting in a peeling action/force that releases and removes the first prosthetic valve 100a from the intermediate layer 704a of the second prosthetic valve 100b. In other examples, the intermediate layer 704a can release from the second prosthetic valve 100b and be removed with the first prosthetic valve 100a.

FIG. 29 shows the second prosthetic valve 100b after the first prosthetic valve 100a has been removed from within the first prosthetic valve 100a with the valve structure 104b in an active state. As shown, part of the valve structure 104b is optionally retained between the intermediate layer 704b and the support structure 102a of the first prosthetic valve 100a such that, upon removal of the first prosthetic valve 100a from the second prosthetic valve 100b, the valve structure 104b is operatively exposed to open and close within the support structure 102b. If desired, the effective inner diameter of the second prosthetic valve 100b defined by the intermediate layer 704b may be close to that of the first prosthetic valve 100a so that a drastic change in inner diameter (e.g., greater than 15%, greater than 20%, or greater than 50%) is not exhibited at the time of removal of the first prosthetic valve 100a. Alternatively, the intermediate layer 704b may be removed at the same time as, or close in time to, the first prosthetic valve 100a.

As an additional feature, if desired, the intermediate layer 704b optionally retains stored portions 608b of the valve structure 104b so that the second prosthetic valve 100b is configured to operate at an inner diameter that is close to that the prosthetic valve 100 operated at prior to removal of the first prosthetic valve 100a. In some examples, the intermediate layer 704b is compressible (e.g., formed of a compressible material) and/or removable over time (e.g., formed of a biodegradable material) to increase the inner diameter of the second prosthetic valve 100b and reveal the stored portions 608b of the valve structure 104b such that the valve structure 104b adjusts in geometry to accommodate the increased inner diameter as shown in FIG. 30.

Any of the features for facilitating diametric adjustment of the first prosthetic valve 100a and/or and second prosthetic valve 100b (fracturable coatings, creep mechanisms, biodegradable features, folds, compression layers, etc.) may additionally or alternatively be employed as desired.

FIGS. 31-34 show additional or alternative diametric expansion features for the prosthetic valve 100. Generally, such features can include a "fish gill" arrangement in which each of the one or more leaflets 106 has multiple, separate components that define overlap regions, where the multiple separate components slide relative to each other during expansion, but remain in an overlapping configuration following expansion to accommodate an increase in diameter of the prosthetic valve 100. In different terms, the components are in operable engagement with one another when the prosthetic valve 100 is at a first diameter at which the prosthetic valve 100 is configured to be implanted to allow fluid flow through the prosthetic valve 100 in a first direction and inhibit fluid flow through the prosthetic valve in an opposite, second direction, and the components are configured to be in operable engagement with one another when the prosthetic valve 100 is at a second diameter that is larger than the first diameter by sliding relative to each other thereby reducing the width of the overlap region as the diameter of the prosthetic valve 100 is increased.

In the example of FIGS. 31-34, there are two overlap regions, one on each side of the leaflet 106, since the expansion of the prosthetic valve 100 is in the radial direction, although any number of components and overlap regions are contemplated in order to accomplish a larger effective leaflet geometry following diametric expansion of the prosthetic valve 100.

As shown in FIG. 31, the one or more leaflets 106 includes cut outs or openings at the first side region 302 and the second side region 304. These cut outs or openings may assist with diametric expansion of each of the leaflets 106, and thus the valve structure 104. For example, the cut outs may act as reliefs that allow outward widening of the leaflets 106.

Each of the one or more leaflets 106 further includes one or more overlap components 106g (FIG. 32). These overlap components 106g (also described as a second component or a gill component) are similarly attached to the support structure (e.g., along an attachment zone 142g at a perimeter of the overlap component 106g). The overlap components 106g are optionally formed of similar materials to the leaflets 106 or different materials as desired. In various examples, the overlap components 106g are able to slide over the leaflets 106 during diametric expansion while still remaining in operable engagement with the leaflets 106 when the valve structure 104 is closed, thus facilitating adjustment of the valve structure 104 to diametric expansion of the prosthetic valve 100. In general terms, the width of the overlap region between the overlap components 106g and the leaflets 106 is reduced as the inner diameter of the prosthetic valve 100 is increased.

As shown in FIG. 33, each of the leaflets 106 acts as a first component and each of the overlap components 106g acts as a second component overlapping a corresponding one of the leaflets 106. FIG. 34 also shows the overlap components 106g interacting with the leaflets 106 as viewed from an interior downstream view of the prosthetic valve 100. In the example shown, there are two overlap components 106g for each of the leaflets 106 corresponding to the first side region 302 and the second side region 304 of the leaflets 106. In this manner, the prosthetic valve 100 includes a first leaflet component in the form of the leaflet 106 and one or more second leaflet components in the form of the overlap components 106g that are disposed downstream of and at least partially overlapping the first leaflet component. The arrangement defines an overlap region between the overlap components 106g and the leaflets 106 that has a width, where the leaflets 106 and the associated overlap components 106g are in operable engagement configured to allow forward fluid flow through the prosthetic valve 100 in a first direction extending downstream and prevent retrograde fluid flow through the prosthetic valve 100 in an opposite direction. Any of a variety of positions of the overlap components 106g is contemplated, including additional or alternative overlap components positioned at the base 150 of the leaflets 106.

Figure 35A:
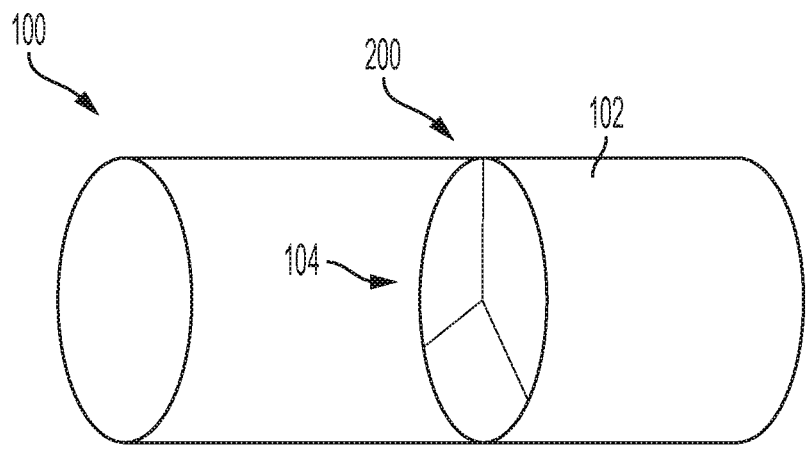
FIGS. 35A and 35B illustrate additional or alternative expansion features for the prosthetic valve, according to some embodiments.
Figure 35B:
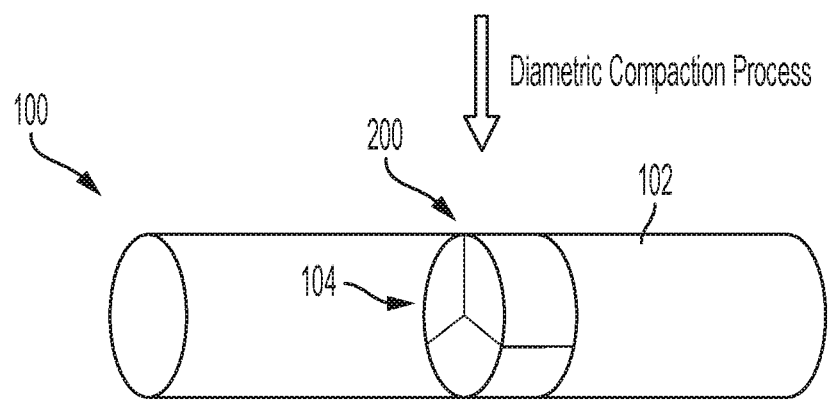

FIGS. 35A-35B are illustrative of a method of forming a prosthetic valve 100 that is diametrically adjustable, according to some examples. As shown in FIG. 35A, the prosthetic valve 100 is initially manufactured at a maximum desired diameter with the valve structure 104 configured to close, or coapt in a desired manner. The prosthetic valve 100 then undergoes a diametric compaction process in which the diameter of prosthetic valve 100, and particularly the diameter of the inner lumen of the prosthetic valve 100, is decreased as shown in FIG. 35B.

As part of the diametric compaction process, portions of the leaflets 106 (e.g., the side regions) are reversibly attached to the inner surface 110 of the prosthetic valve 100 such that the unbonded leaflet portions, or free leaflet portions are retained at a desired size for the smaller diameter that permits coaptation of the valve structure 104. Leaflet attachment may be achieved via a variety of means, including utilizing heat treatments, fluoropolymer adhesives/materials (e.g., FEP, PATT, PATT-OH, low-melt FEP, or others), or by other means.

In some examples, the diameter of prosthetic valve 100, and in particular the support structure 102, is decreased as part of a material retraction process. For example, where the support structure is formed of a material including a fibril structure (e.g., ePTFE) a process of forming bent or S-shaped fibrils can be employed via retraction of the fibril structure and a coating of an elastomeric material (e.g., FEP). Examples of suitable retraction processes and materials can be found in U.S. Pat. No. 9,522,072 to Kovach et al., filed by W.L. Gore & Associates, Inc. on Mar. 6, 2014.

In some examples, unwanted-, or over-dilation, of the prosthetic valve 100 when transitioning back from the diametrically compacted state to the diametrically enlarged state can be prevented by providing the prosthetic valve 100 with a film that provides a relatively high elongation resistance in a circumferential direction of the prosthetic valve 100 when the prosthetic valve 100 is at the enlarged diameter.

The prosthetic valve 100 is configured to be diametrically enlarged while maintaining the ability of the valve structure 104 to properly coapt. In order to facilitate such adjustability, as a general matter, often times there is a leaflet bonding length to diametric compaction ratio of the support structure that provides the ability of the valve structure 104 to coapt at a desired diameter. In some examples, the valve structure 104 resists tensile deformation such that, upon diametric expansion of the prosthetic valve 100, portions of the valve structure 104 that are secured to the support structure 102 pull away from the support structure and are freed, or released, to accommodate the increase in diameter and maintain the ability to coapt properly. In some implementations, the prosthetic valve 100 is able to be adjusted over a wide range of diameters with the valve structure 104 freeing itself from the support structure 102 along with the diametric expansion, and thus permitting the valve structure 104 to properly coapt at a variety of increasing diameters to which the prosthetic valve 100 is adjusted.

The foregoing examples have largely been described without regard to an associated frame, such as those commonly employed in surgical prosthetic valves or transcatheter prosthetic valves. As previously referenced, the prosthetic valve 100 according to any of the preceding examples optionally includes an adjustable frame (not shown). In various examples, the adjustable frame has adjustment features, such as zig-zags or bends, that allow for expansion; sliding components that allow for frame expansion and resist collapse with ratchets or stops, for example; frangible elements that fracture to allow for self-expansion; inner and outer frame components, where the outer frame is diametrically adjustable with sufficient resistance to collapse to provide support at both smaller and larger diameters, or other adjustment features, including any of those described below.

FIGS. 36-39 show a prosthetic valve 1100 according to various examples. The prosthetic valve 1100 includes an adjustable frame 1102, also described as a support structure 1102, and a valve structure 1104 including one or more leaflets 1106 (individually referred to as 1106a, 1106b, 1106c). In some examples, the prosthetic valve 1100 can be increased in diameter by a factor of two, for example, although any of a variety of diametric adjustment factors are contemplated.

Features of the prosthetic valve 1100 may be employed in any of a variety of applications, including pulmonary valve conduits, surgical or transcatheter mitral, aortic, or other valve repair, or non-cardiac applications as desired. For example, features of the adjustable frame 1102 are optionally used with the support structure 102 of the prosthetic valve 100 of any of the preceding examples (e.g., in a pulmonary valve conduit application). Similarly, any of the features of the valve structure 104 or other features according to the preceding examples may be employed with the prosthetic valve 1100 as desired.

The adjustable frame 1102 includes a plurality of frame elements 1120a, 1120b, 1120c (or collectively, 1120). As shown, the frame elements 1120 are axi-symmetric in that they are generally similar to one another are arranged in an in an equal and opposing manner. Although three elements are shown, any number (greater or fewer) is contemplated.

FIG. 37 is a schematic view of one of the frame elements 1120 (the frame element 1120a) for illustration purposes. As shown, the frame element 1120a includes a top rail 1122a, a bottom rail 1124a, a leaflet payout edge support 1126a, a primary leaflet edge support 1128a, and a secondary leaflet edge support 1130a. Each of the frame elements 1120 includes tabs 1150 for slidably engaging the other frame elements 1120 (e.g., on the top rails and bottom rails of the frame elements 1120).

The tabs 1150 are optionally in the form of hooks, clasps, or other features that can couple and slide with adjacent frame elements 1120. In some examples, the tabs 1150 and/or the frame elements 1120 include retaining features (e.g., stops, ratchets, detents, or other features) that stop relative sliding of the frame elements 1120 at pre-selected locations. In some examples, such features help ensure that the frame elements 1120 adjust uniformly and equally to a desired diametric adjustment setpoint, helping to ensure a regular geometry is imparted on the valve structure 1104 at one or more diametric setpoints. In some examples, the tabs 1150 themselves can serve as stops by interlocking with one another, abutting one another, or otherwise interacting with one another. FIGS. 43-45, which are referenced below, illustrate some examples of retaining features for facilitating adjustment of the prosthetic valve 1100 to diametric setpoints, according to some examples.

As described further below, each of the leaflets 1106 is secured to a respective one of the frame elements 1120 in a manner that permits leaflet material to be stored when the prosthetic valve 1100 is a first diameter and then paid out to enlarge the size of the valve structure 104 as the adjustable frame 1102 is enlarged. With the example of the frame element 1120a, the material of the corresponding leaflet 1106 is secured to the leaflet payout edge support 1126a and the primary leaflet edge support 1128a. As described in further detail below, the primary leaflet edge support 1128a serves to define an operative edge of the leaflet 1106a and another one of the frame elements 1120 (e.g., frame element 1120b) serves to define an opposite, operative edge of the leaflet 1106a.

FIGS. 38 and 39 are flat, schematic views illustrating relative sliding action between the frame element 1120a and the frame element 1120b, and the concomitant adjustment of the operative geometry of the leaflet 1106a (the operative geometry, or the area of the leaflet that is active and actuable during valve opening and closing, is indicated by cross-hatching on FIGS. 38-39). It should be noted that FIGS. 37-39 are flat representations for illustration purposes and that the frame elements 1120 are actually arranged to define a three-dimensional, circular structure as shown in FIG. 36, for example.

As shown in the schematic view of FIG. 38, the primary leaflet edge support 1128a of the frame element 1120a defines a first operative edge 1160a of the leaflet 1106a and the secondary leaflet edge support 1130b of the frame element 1120b defines a second operative edge 1162a of the leaflet 1106a.

As shown in FIG. 39, as the frame element 1120a is slid relative to the frame element 1120b (as would occur during diametric expansion of the adjustable frame 1102), the primary leaflet edge support 1128a of the frame element 1120a slides away from the secondary leaflet edge support 1130b of the frame element 1120b, and the material of the leaflet 1106a slides over the secondary leaflet edge support 1130b, exposing additional material to the interior of the prosthetic valve 1100 to define a larger operative geometry for the leaflet 1106a. In different terms, the secondary leaflet edge support 1130b is not fixedly secured to the material of the leaflet 1106a, but instead acts as an adjustable support for the second operative edge 1162a.

Figure 42:
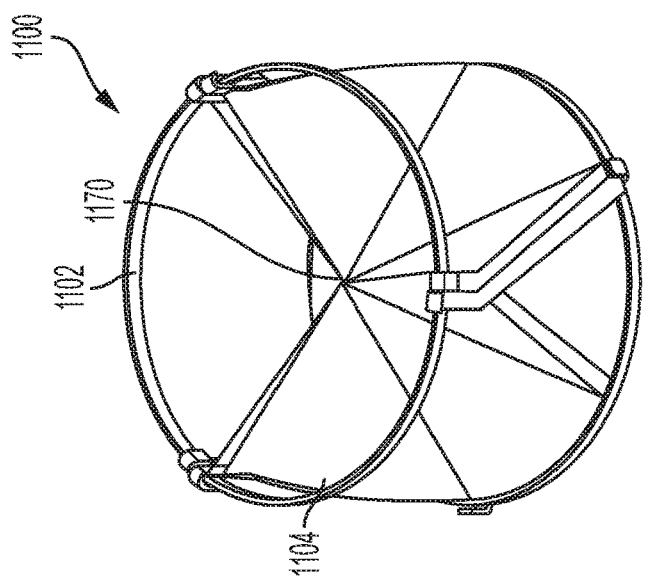
Figure 41:
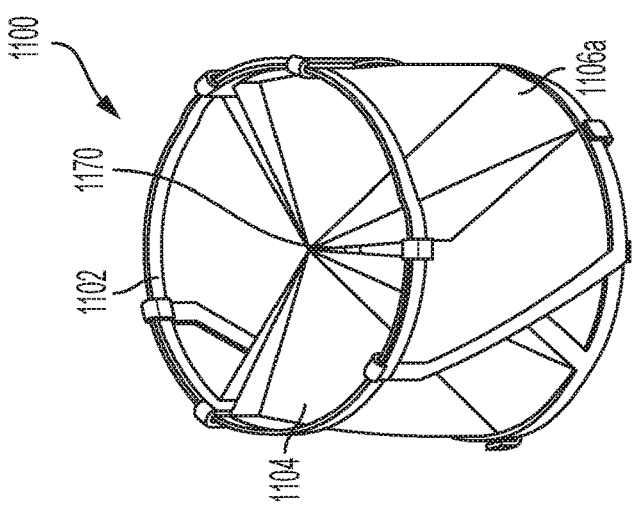
Figure 40:
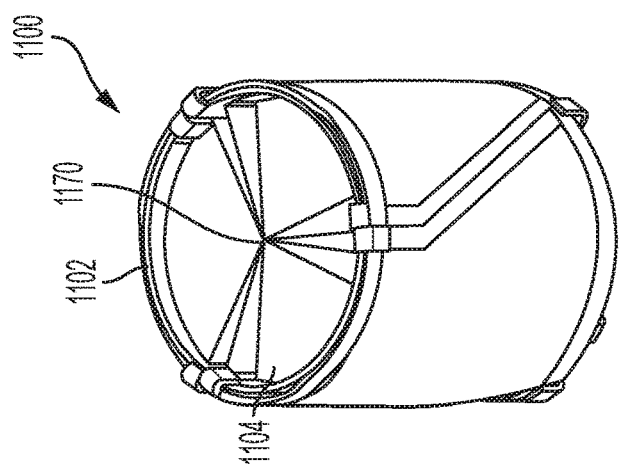
Figure 46:
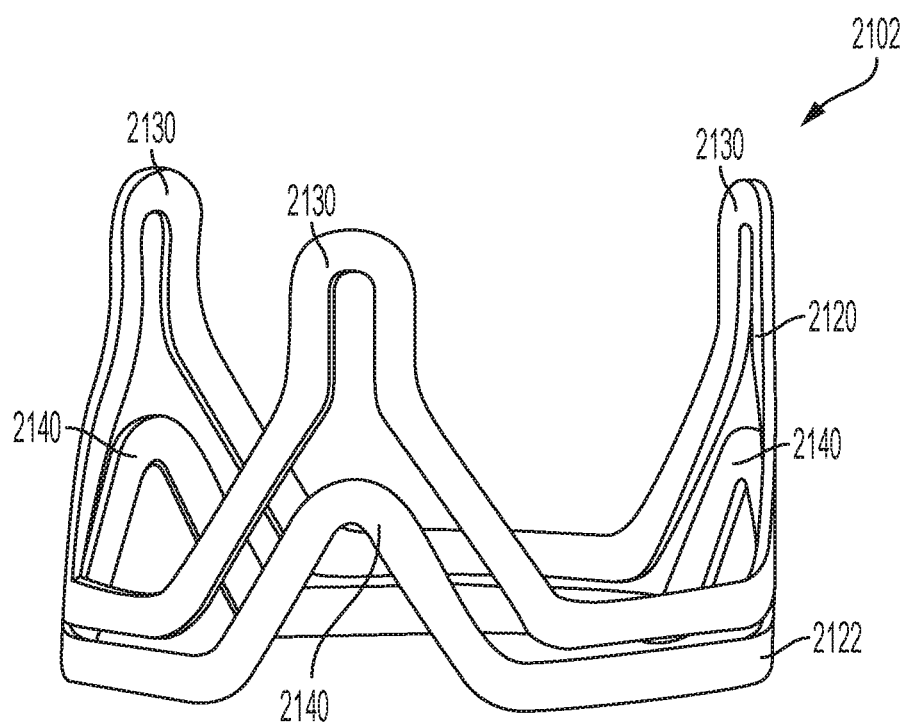
FIGS. 46-52 illustrate a diametrically expandable prosthetic valve, according to some embodiments.

This sliding arrangement between the frame elements 1120 and the concomitant adjustment of the operative geometry of the leaflets 1106 can be further observed with reference to FIGS. 40-42, which show the prosthetic valve 1100 transitioning from a first, smaller diameter (FIG. 40) to a second, intermediate diameter (FIG. 41), and then to an enlarged (e.g., final) diameter (FIG. 42). As indicated in FIG. 41 by a white arrow, the material of the leaflet 1106a is paid out from the circumference of the prosthetic valve 1100 during adjustment to increase the operative geometry of the leaflet 1106a during expansion.

Described in different terms, the frame elements 1120 slide over one another to allow more of the stored or hidden material of the leaflets 1106 ("hidden" in the sense it is not exposed for purposes of actuation during opening and closing) to become the active, actuable part of the leaflets 1106. This feature helps allows the diameter of the prosthetic valve 1100 to increase and allow the leaflets 1106 to function efficiently. The ability to pay out, or release additional leaflet material helps allow the leaflets 1106 to coapt and seal at various frame diameters while minimizing redundant (or extra) material that might otherwise be present at the point where the leaflets 1106 meet, or convergence of the leaflets 1106 (e.g., the triple point), if the full width of leaflet material were made available at all diameters. Such extra material at the convergence of the leaflets 1106 may be undesirable in that extra material can cause the leaflets not to open fully or smoothly at the convergence of the leaflets 1106.

The operative leaflet geometries of the leaflets 1106 are defined by the frame element 1120 to which the leaflet 1106 is attached and by an adjacent one of the frame elements 1120. The relative sliding motion of the frame elements 1120, and the payout of leaflet material defining the active portion of the leaflets 1106, allows the operative edges (or the leaflet attachment lines) of each of the leaflets 1106 to remain constant over the entire range of diametric adjustment. As will be noted on FIGS. 40-42, a distance from the bases of the leaflets 1106 to a center 1170 of the valve structure 1104 (e.g., the "triple point" as shown), remains constant so the center 1170 drops, or moves down vertically relative to the remainder of the prosthetic valve 1100 as the prosthetic valve 1100 increases in size diametrically.

FIGS. 43-45 show examples of retaining features that are optionally employed to control sliding of the frame elements 1120 relative to one another. For example, as shown in FIG. 43, one or more of the frame elements 1120 optionally include a plurality of ratchet protections, or teeth 1120r and the tabs 1150 include a pawl 1150p that permits sliding between the frame element 1120 and the tab 1150 in a first direction but resists or stops relative sliding in the opposite direction. FIGS. 44-45 show another retaining feature option. As shown in FIG. 44, the tab 1150 is in the form of a hook with an inward protection 1150p that is configured as a catch, dog, or spring-operated ball, for example. FIG. 45 shows a frame element 1102 with a plurality of seats, or receivers 1120r along the frame element 1120. The inward projection 1150p optionally retains the tab 1150 at a desired location along the frame element 1120 and is disengaged and allowing further sliding of the tab 1150 along the frame element 1120 (e.g., during diametric expansion of the valve 100) upon exceeding a particular retaining force between the above-referenced retaining features.

FIGS. 46-52 show an adjustable frame 2102 of a prosthetic valve according to various examples. Features of the adjustable frame 2102 may be employed in any of a variety of applications, including pulmonary valve conduits, surgical or transcatheter mitral, aortic, or other valve repair, or non-cardiac applications as desired. For example, features of the adjustable frame 2102 are optionally used with the support structure 102 of the prosthetic valve 100 of any of the preceding examples (e.g., in a pulmonary valve conduit application) and the adjustable frame 1102 of any of the preceding examples. If desired, the adjustable frame 2102 is configured for implantation via a surgical technique, and can then later be diametrically adjusted to a larger diameter (e.g., using a transcatheter balloon technique) and a second, larger diameter prosthetic valve (not shown) can be implanted within the adjustable frame 2102. Additionally, the adjustable frame 2102 may be dilated (diametrically adjusted) with an associated valve structure (not shown) configured to adjust to the increased diameter (such as a valve structure having any of the features previously described).

As shown the adjustable frame 2102 includes a first frame element 2120 and a second frame element 2122. The first frame element 2120 is optionally configured to support and be coupled to a valve structure (not shown) and includes a plurality of split commissure posts 2130. In some examples, the split commissure posts 2130 may provide the ability to plastically deform the first frame element 2120 and increase the diameter of the first frame element 2120. However, such an arrangement may also result in reduced resistance to compression of the first frame element 2120 under physiologic loading. Regardless, in various examples the first frame element 2120, which supports a valve structure, is diametrically expandable, but may benefit from diametric reinforcement during operation and/or following diametric expansion.

The second frame element 2122 is optionally secured to the first frame element 2120 (e.g., using one or more layers of film material or other material) to reinforce the first frame element 2120 resistance to compression. As shown, the second frame element 2122 optionally includes a plurality of selective expansion features 2140. As shown, the selective expansion features 2140 form an apex, or "A" shape that allows diametric expansion when a sufficient expansion force is exerted on the frame (e.g., using a balloon catheter). As the apex, or A shape elongates or widens with expansion, the shape becomes flatter and more elongate, and naturally becomes more resistant to compressive forces on the second frame element 2122. This, in turn, reinforces the first frame element 2120 by virtue of its connection to the second frame element 2122 (this connection is not shown, but is optionally accomplished via film as previously described or other means as desired).

Figure 48:
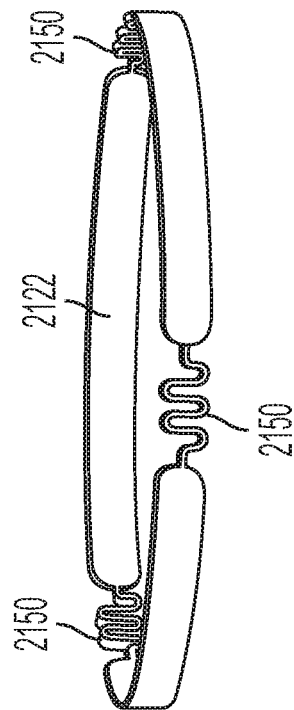
Figure 47:
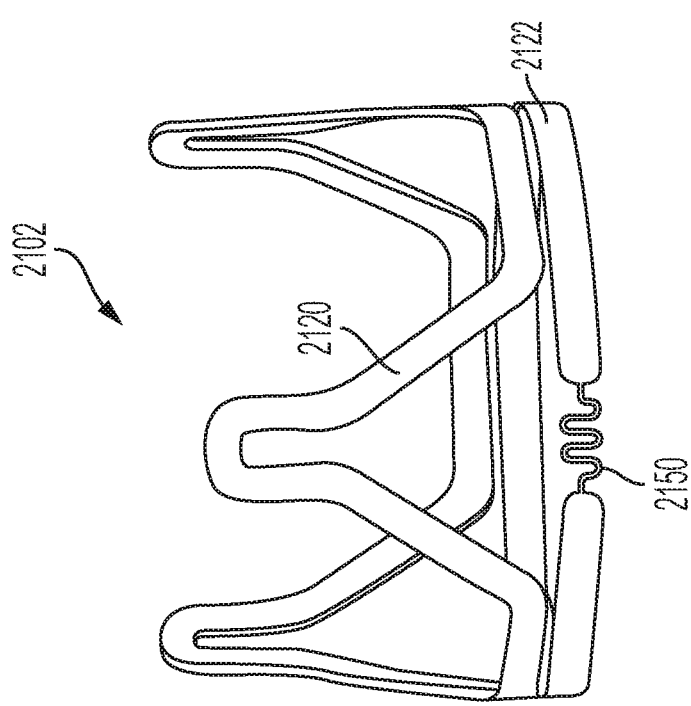
Figure 49:
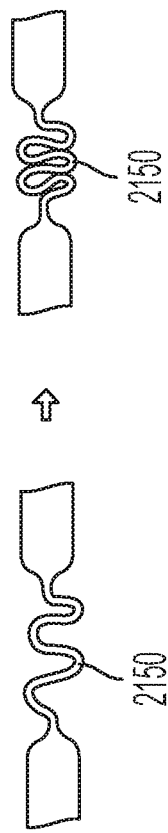

FIGS. 47 and 48 show alternative or additional selective expansion features 2150 in the form of an undulating, or sinusoidal shaped elements. These selective expansion features 2150 that naturally resist further compression at the initial, smaller diameter. In particular, the selective expansion features 2150 bottom out or self-limit (e.g., the selective expansion features 2150 include surfaces that engage each other) to inhibit further compression. This self-limiting attribute of the selective expansion features 2150 is illustrated generally in FIG. 49 where the sketch on the left shows one of the selective expansion features 2150 prior to compression and the sketch on the right shows one of the selective expansion features 2150 self-limiting and providing a natural stop against further diametric compression. Upon diametric expansion, the selective expansion features 2150 can straighten. Upon straightening (or reducing the degree of undulation), the selective expansion features 2150 provide enhanced resistance to compression back from the expanded diameter. In different terms, the more straight, and less undulating shape, results in less perpendicular forces on the arrangement from compression and instead achieve more oblique compression angles on the selective expansion features 2150.

Figure 52:
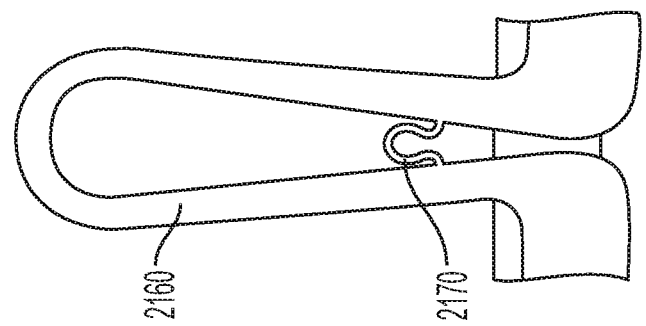
Figure 51:
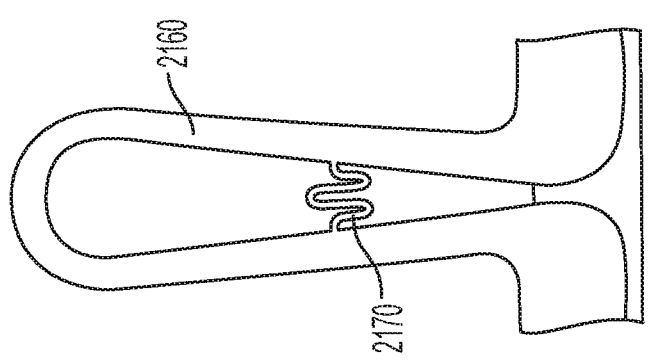
Figure 50:
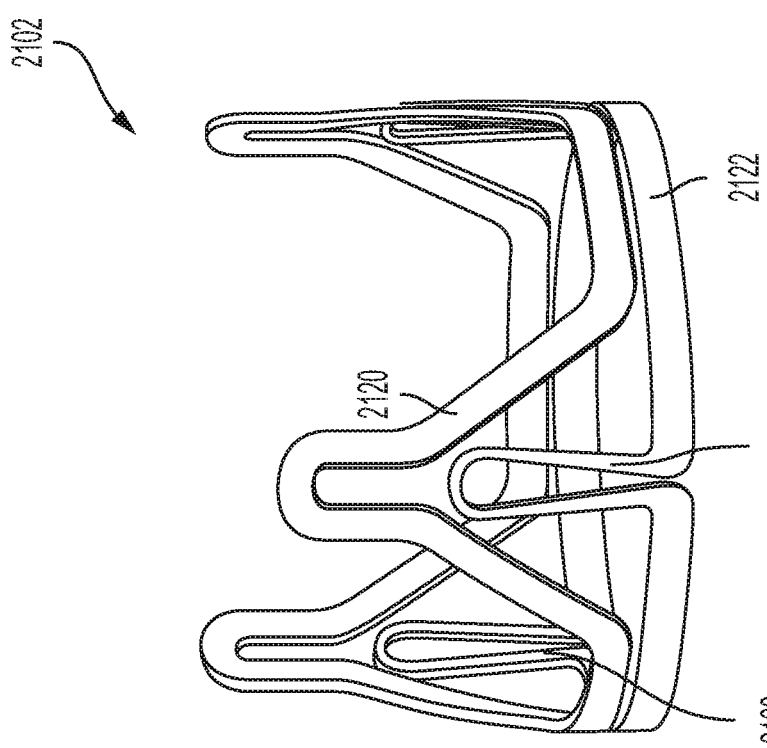

FIGS. 50-52 show alternative or additional selective expansion features 2160 in the form of high arch, or omega-shaped elements. These selective expansion features 2160 naturally resist further compression at the initial, smaller diameter. In particular, the selective expansion features 2160 also bottom out or self-limit (e.g., the selective expansion features 2150 include surfaces that engage each other) to inhibit further compression. As shown, the bases of the arch shapes will come into contact to arrest compression of the second frame element 2122. The relatively long arc-length of the curvature of the arch-shape of the selective expansion features 2160 may help spread stresses/strains over a greater area, thereby helping resist fatigue effects. Additionally, such distributed stress/strain profiles may assist with resisting compression following diametric expansion by distributing strain hardening across the apex of the arch-, or omega-shaped selective expansion features 2160.

FIGS. 51-52 show additional variations of the selective expansion features 2160. As shown, auxiliary expansion features 2170 may be coupled between portions of the selective expansion features 2160. For example, auxiliary expansion features shaped similarly to the selective expansion features 2150 (FIG. 51) and/or the selective expansion features 2160 (FIG. 52) may be coupled to the auxiliary expansion features 2170 (e.g., between the legs of the arch shape). These auxiliary expansion features 2170 operate in a similar manner to resist compression at the initial, smaller diameter (e.g., by self-engaging), permit expansion to a larger diameter (e.g., by deforming), and then resist compression at the larger diameter (e.g., by straightening).

Inventive features of this disclosure have been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A prosthetic valve comprising:
   one or more primary leaflets each defining a primary leaflet base, a primary leaflet free edge, a primary leaflet first commissure region, a primary leaflet second commissure region, and a primary leaflet belly region; and
   one or more auxiliary leaflets stored in an inactive state, each of the one or more auxiliary leaflets defining an auxiliary leaflet base, an auxiliary leaflet free edge, an auxiliary leaflet first commissure region, an auxiliary leaflet second commissure region, and an auxiliary leaflet belly region, the one or more auxiliary leaflets being configured to release to an active state upon diametrically expanding the prosthetic valve.

2. The prosthetic valve of claim 1, wherein the one or more auxiliary leaflets are stored in the inactive state by one or more folds formed by the one or more primary leaflets, the one or more folds of the primary leaflets being releasably secured in a folded configuration and configured to be released from the folded configuration upon diametrically expanding the prosthetic valve to transition the auxiliary leaflets to the active state.

3. The prosthetic valve of claim 2, wherein at least one of the primary leaflets includes a first side region, a second side region, and a central region located between the first and second side regions, and wherein the one or more folds are formed in at least one of the first side region, the second side region, and the central region.

4. The prosthetic valve of claim 2, wherein the one or more folds formed by the one or more primary leaflets are releasably secured in the folded configuration by a coating, an adhesive, a thermal bond, a mechanical fastener, or combinations thereof.

5. The prosthetic valve of claim 2, wherein the one or more folds formed by the one or more primary leaflets are releasably secured in the folded configuration such that the folds formed by the primary leaflets are configured to be released from the folded configuration upon an expansion force being imparted on the prosthetic valve and/or fallowing an extended period of time.

6. The prosthetic valve of claim 2, wherein the one or more primary leaflets include a pair of adjacent primary leaflets and the one or more folds formed by the primary leaflets are positioned at a location corresponding to a commissure region between pair of adjacent primary leaflets.

7. The prosthetic valve of claim 1, wherein the prosthetic valve includes a support structure to which the one or more primary leaflets are coupled.

8. The prosthetic valve of claim 7, wherein the support structure includes a tubular conduit.

9. The prosthetic valve of claim 7, wherein the support structure includes a frame.

10. The prosthetic valve of claim 7, wherein the one or more auxiliary leaflets are stored in the inactive state by one or more folds formed by the support structure, the folds of the support structure each being releasably secured in a folded configuration and configured to be released from the folded configuration upon diametrically expanding the prosthetic valve to transition the auxiliary leaflets to the active state.

11. The prosthetic valve of claim 10, wherein the one or more folds formed by the support structure are releasably secured in the folded configuration by a coating, an adhesive, a thermal bond, a mechanical fastener, or combinations thereof.

12. The prosthetic valve of claim 10, wherein the one or more folds formed by the support structure are releasably secured in the folded configuration such that the folds formed by the support structure are configured to release from the folded configuration upon an expansion force being imparted on the prosthetic valve and/or following an extended period of time.

13. The prosthetic valve of claim 10, wherein the one or more primary leaflets include a pair of adjacent primary leaflets and the one or more folds formed by the support structure are positioned at a location along the support portion corresponding to a commissure region between the pair of adjacent primary leaflets.

14. The prosthetic valve of claim 1, wherein the primary leaflets include a pair of adjacent, primary leaflets coupled to a splittable commissure support, and further wherein one of the auxiliary leaflets is coupled to the splittable commissure support such that the auxiliary leaflet is transitionable from the stored, inactive state to the released, active state upon diametrically expanding the prosthetic valve to split the splittable commissure support.

15. The prosthetic valve of claim 14, wherein the splittable commissure support is releasably secured together by a coating, an adhesive, a thermal bond, a mechanical fastener, or combinations thereof.

16. The prosthetic valve of claim 14, wherein the releasable commissure support is configured to be released and split upon an expansion force being imparted on the prosthetic valve and/or following an extended period of time.

17. The prosthetic valve of claim 1, wherein the prosthetic valve has a first operative diameter at which the prosthetic valve is configured to be implanted and a second operative diameter that is larger than the first operative diameter to which the prosthetic valve is configured to be diametrically adjusted, and further wherein the one or more of primary leaflets are operable to move between open and closed positions to allow and inhibit flow, respectively, through the prosthetic valve such that the primary leaflets are configured in an active state, and further wherein the prosthetic valve is configured such that upon transitioning to the second operative diameter the one or more auxiliary leaflets are transitioned to the active state such that the auxiliary leaflets are operable to move between open and closed positions to allow and inhibit flow, respectively, through the prosthetic valve.

18. The prosthetic valve of claim 17, wherein the one or more primary leaflets are configured to be in the active state when the prosthetic valve is at the second operative diameter.

19. A method of making a prosthetic valve, the method comprising:
   forming a valve structure including one or more primary leaflets each defining a primary leaflet base, a primary leaflet free edge, a primary leaflet first commissure region, a primary leaflet second commissure region, and a primary leaflet belly region, and one or more auxiliary leaflets each of the one or more auxiliary leaflets defining an auxiliary leaflet base, an auxiliary leaflet free edge, an auxiliary leaflet first commissure region, an auxiliary leaflet second commissure region, and an auxiliary leaflet belly region;
   associating the valve structure with a support structure; and storing the one or more auxiliary leaflets in an inactive state such that the one or more auxiliary leaflets are configured to release to an active state upon diametrically expanding the prosthetic valve.

20. A method of treatment of a body conduit of a patient susceptible to changes in diameter over time, the method comprising:

delivering a prosthetic valve to a treatment site for a body conduit, the prosthetic valve having a first operative diameter including one or more primary leaflets of the prosthetic valve being operable to move between open and closed positions to allow and inhibit flow, respectively, through the prosthetic valve such that the primary leaflets are configured in an active state when the prosthetic valve is at the first operative diameter, the first operative diameter further including one or more auxiliary leaflets of the prosthetic valve being stored in an inactive state in which the auxiliary leaflets are inoperable to inhibit flow through the valve, each of the one or more primary leaflets defining a primary leaflet base, a primary leaflet free edge, a primary leaflet first commissure region, a primary leaflet second commissure region, and a primary leaflet belly region, and each of the one or more auxiliary leaflets defining an auxiliary leaflet base, an auxiliary leaflet free edge, an auxiliary leaflet first commissure region, an auxiliary leaflet second commissure region, and an auxiliary leaflet belly region; and securing the prosthetic valve at the treatment site.

21. The method of claim 20, further comprising diametrically adjusting the prosthetic valve implanted in the patient to a second operative diameter including the one or more auxiliary leaflets being transitioned from the inactive state to an active state in which the one or more auxiliary leaflets are operable to move between open and closed positions to allow and inhibit flow, respectively, through the prosthetic valve.

22. A prosthetic valve, comprising:

a first leaflet component having one or more openings defining one or more relief features configured to facilitate outward widening of the first leaflet component; and a second leaflet component at least partially overlapping the one or more relief features of the first leaflet component and defining an overlap region with the first leaflet component having a width, the first leaflet component and the second leaflet component configured to be in operable engagement with one another when the prosthetic valve is at a first diameter at which the prosthetic valve is configured to be implanted to allow fluid flow through the prosthetic valve in a first direction and inhibit fluid flow through the prosthetic valve in an opposite, second direction, and the first leaflet component and the second leaflet component being configured to be in operable engagement with one another when the prosthetic valve is at a second diameter that is larger than the first diameter by sliding relative to each other thereby reducing the width of the overlap region as the diameter of the prosthetic valve is increased, such that the first and second leaflet components allow fluid flow through the prosthetic valve in the first direction and inhibit fluid flow through the prosthetic valve in the opposite, second direction when the prosthetic valve is at the second, larger diameter.

* * * * *